(12) United States Patent
Debus et al.

(10) Patent No.: US 10,829,539 B2
(45) Date of Patent: Nov. 10, 2020

(54) PRODUCTION OF RECOMBINANT VON WILLEBRAND FACTOR IN A BIOREACTOR

(71) Applicant: CSL LIMITED, Parkville, Victoria (AU)

(72) Inventors: Stefan Debus, Gladenbach (DE); Holger Lind, Marburg (DE)

(73) Assignee: CSL Limited, Parkville (AU)

(*) Notice: Subject to any disclaimer, the term of this patent is extended or adjusted under 35 U.S.C. 154(b) by 129 days.

(21) Appl. No.: 15/316,870

(22) PCT Filed: Apr. 14, 2015

(86) PCT No.: PCT/AU2015/050170
§ 371 (c)(1),
(2) Date: Dec. 7, 2016

(87) PCT Pub. No.: WO2015/188224
PCT Pub. Date: Dec. 17, 2015

(65) Prior Publication Data
US 2017/0129938 A1    May 11, 2017

(30) Foreign Application Priority Data
Jun. 13, 2014  (EP) .................................... 14172338

(51) Int. Cl.
*C07K 14/755* (2006.01)
*C07K 1/34* (2006.01)
*C12P 21/02* (2006.01)

(52) U.S. Cl.
CPC ............ *C07K 14/755* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 4,751,180 A | 6/1988 | Cousens et al. | |
| 4,935,233 A | 6/1990 | Bell et al. | |
| 5,872,099 A | 2/1999 | Fischer et al. | |
| 2006/0216790 A1 | 9/2006 | Knudsen | |
| 2009/0192076 A1* | 7/2009 | Matthiessen | A61K 9/0019 514/1.1 |

FOREIGN PATENT DOCUMENTS

| | | |
|---|---|---|
| EP | 0 705 846 A1 | 4/1996 |
| EP | 2 171 034 B1 | 10/2011 |
| WO | WO 98/38219 | 9/1998 |
| WO | WO 2005/024044 A2 | 3/2005 |
| WO | WO 2006/071801 A2 | 7/2006 |
| WO | WO 2008/006494 A1 | 1/2008 |
| WO | WO 2008/152075 A1 | 12/2008 |
| WO | WO 2009/156137 A1 | 12/2009 |
| WO | WO 2010/025278 A1 | 3/2010 |
| WO | WO 2010/048275 A2 | 4/2010 |
| WO | WO 2011/022657 A1 | 2/2011 |
| WO | WO-2011012725 A1 * | 2/2011 ............... C12N 7/00 |
| WO | WO 2012/006591 A1 | 1/2012 |

OTHER PUBLICATIONS

GE Healthcare Selection Handbook: Hollow fiber cartridges and systems for membrane separations 20080: 93 pages. (Year: 2008).*
Beattie et al., "Structure and evolution of human α-fetoprotein deduced from partial sequence of closed cDNA," Gene, 20 (1982), pp. 415-422.
Cooke et al., "Serum vitamin D-binding protein is a third member of the albumin and alpha fetoprotein gene family," J Clin Invest., vol. 76, Dec. (1985), pp. 2420-2424.
Maratea et al., "Deletion and fusion of the phage φX174 lysis gene E," Gene, 40 (1985), pp. 39-46.
Murphy et al., "Genetic construction, expression, and melanoma-selective cytotoxicity of a diphtheria toxin-related α-melanocyte-stimulating hormone fusion protein," Proc. Natl. Acad. Sci. USA, Nov. 1986, vol. 83, pp. 8258-8262.
Lichenstein et al., "Afamin is a new member of the albumin, α-fetoprotein, and vitamin d-binding protein gene family," The Journal of Biological Chemistry, vol. 269, No. 27, Jul. 8, 1994, pp. 18149-18154.
Fischer, "Recombinant von Willebrand factor: potential therapeutic use," Journal of Thrombosis and Thrombolysis, 1999, vol. 8, pp. 197-205.
Kallas et al., "The von Willebrand factor collagen-binding activity assay: clinical application," Ann Hematol (2001) vol. 80, pp. 466-471.
Veronese, "Introduction and overview of peptide and protein pegylation," Advanced Drug Delivery Reviews, vol. 54 (2002), pp. 453-456.
Federici et al., "A sensitive ristocetin co-factor activity assay with recombinant glycoprotein Ibα for the diagnosis of patients with low von Willebrand factor levels," Haematologica (2004) vol. 89, pp. 77-85.

(Continued)

*Primary Examiner* — Marsha Tsay

(74) *Attorney, Agent, or Firm* — Finnegan, Henderson, Farabow, Garrett & Dunner LLP

(57) ABSTRACT

The present invention relates to improved methods for the recombinant production of von Willebrand factor (vWF) in a bioreactor by separating different multimeric forms of vWF with different molecular weight during fermentation.

12 Claims, 9 Drawing Sheets
Specification includes a Sequence Listing.

(56) References Cited

OTHER PUBLICATIONS

Sucker et al., "Determination of von Willebrand factor activity: evaluation of the HaemosIL™ assay in comparison with established procedures," Clinical and Applied Thrombosis/Hemostasis, vol. 12, No. 3, Jul. 2006, pp. 305-310.

Ott et al., "Analysis of von Willebrand factor multimers by simultaneous high- and low-resolution vertical SDS-agarose gel electrophoresis and Cy5-labeled antibody high-sensitivity fluorescence detection," American Society for Clinical Pathology, (2010) vol. 133, pp. 322-330.

International Search Report, dated Jun. 26, 2015, in International Patent Application No. PCT/AU2015/050170, 8 pages.

Written Opinion of International Search Report, dated Jun. 26, 2015, in International Patent Application No. PCT/AU2015/050170, 4 pages.

\* cited by examiner

SEQUENCE LISTING

<160> NUMBER OF SEQ ID NOS: 3

<210> SEQ ID NO 1
<211> LENGTH: 8442
<212> TYPE: DNA
<213> ORGANISM: Homo sapiens
<220> FEATURE:
<221> NAME/KEY: CDS
<222> LOCATION: (1)..(8442)

<400> SEQUENCE: 1

```
atg att cct gcc aga ttt gcc ggg gtg ctg ctt gct ctg gcc ctc att      48
Met Ile Pro Ala Arg Phe Ala Gly Val Leu Leu Ala Leu Ala Leu Ile
1               5                   10                  15 ttg cca ggg acc ctt tgt gca gaa gga act cgc ggc agg tca tcc acg      96
Leu Pro Gly Thr Leu Cys Ala Glu Gly Thr Arg Gly Arg Ser Ser Thr
            20                  25                  30 gcc cga tgc agc ctt ttc gga agt gac ttc gtc aac acc ttt gat ggg     144
Ala Arg Cys Ser Leu Phe Gly Ser Asp Phe Val Asn Thr Phe Asp Gly
        35                  40                  45 agc atg tac agc ttt gcg gga tac tgc agt tac ctc ctg gca ggg ggc     192
Ser Met Tyr Ser Phe Ala Gly Tyr Cys Ser Tyr Leu Leu Ala Gly Gly
    50                  55                  60 tgc cag aaa cgc tcc ttc tcg att att ggg gac ttc cag aat ggc aag     240
Cys Gln Lys Arg Ser Phe Ser Ile Ile Gly Asp Phe Gln Asn Gly Lys
65                  70                  75                  80 aga gtg agc ctc tcc gtg tat ctt ggg gaa ttt ttt gac atc cat ttg     288
Arg Val Ser Leu Ser Val Tyr Leu Gly Glu Phe Phe Asp Ile His Leu
                85                  90                  95 ttt gtc aat ggt acc gtg aca cag ggg gac caa aga gtc tcc atg ccc     336
Phe Val Asn Gly Thr Val Thr Gln Gly Asp Gln Arg Val Ser Met Pro
            100                 105                 110 tat gcc tcc aaa ggg ctg tat cta gaa act gag gct ggg tac tac aag     384
Tyr Ala Ser Lys Gly Leu Tyr Leu Glu Thr Glu Ala Gly Tyr Tyr Lys
        115                 120                 125 ctg tcc ggt gag gcc tat ggc ttt gtg gcc agg atc gat ggc agc ggc     432
Leu Ser Gly Glu Ala Tyr Gly Phe Val Ala Arg Ile Asp Gly Ser Gly
    130                 135                 140 aac ttt caa gtc ctg ctg tca gac aga tac ttc aac aag acc tgc ggg     480
Asn Phe Gln Val Leu Leu Ser Asp Arg Tyr Phe Asn Lys Thr Cys Gly
145                 150                 155                 160 ctg tgt ggc aac ttt aac atc ttt gct gaa gat gac ttt atg acc caa     528
Leu Cys Gly Asn Phe Asn Ile Phe Ala Glu Asp Asp Phe Met Thr Gln
                165                 170                 175 gaa ggg acc ttg acc tcg gac cct tat gac ttt gcc aac tca tgg gct     576
Glu Gly Thr Leu Thr Ser Asp Pro Tyr Asp Phe Ala Asn Ser Trp Ala
```

-continued

|  |  |  |  |  |  |  |  |  |  |  |  |  |  |  |  |
|---|---|---|---|---|---|---|---|---|---|---|---|---|---|---|---|
|  | 180 |  |  |  | 185 |  |  |  | 190 |  |  |  |  |  |  |

```
ctg agc agt gga gaa cag tgg tgt gaa cgg gca tct cct ccc agc agc      624
Leu Ser Ser Gly Glu Gln Trp Cys Glu Arg Ala Ser Pro Pro Ser Ser
        195                 200                 205 tca tgc aac atc tcc tct ggg gaa atg cag aag ggc ctg tgg gag cag      672
Ser Cys Asn Ile Ser Ser Gly Glu Met Gln Lys Gly Leu Trp Glu Gln
210                 215                 220 tgc cag ctt ctg aag agc acc tcg gtg ttt gcc cgc tgc cac cct ctg      720
Cys Gln Leu Leu Lys Ser Thr Ser Val Phe Ala Arg Cys His Pro Leu
225                 230                 235                 240 gtg gac ccc gag cct ttt gtg gcc ctg tgt gag aag act ttg tgt gag      768
Val Asp Pro Glu Pro Phe Val Ala Leu Cys Glu Lys Thr Leu Cys Glu
                245                 250                 255 tgt gct ggg ggg ctg gag tgc gcc tgc cct gcc ctc ctg gag tac gcc      816
Cys Ala Gly Gly Leu Glu Cys Ala Cys Pro Ala Leu Leu Glu Tyr Ala
        260                 265                 270 cgg acc tgt gcc cag gag gga atg gtg ctg tac ggc tgg acc gac cac      864
Arg Thr Cys Ala Gln Glu Gly Met Val Leu Tyr Gly Trp Thr Asp His
        275                 280                 285 agc gcg tgc agc cca gtg tgc cct gct ggt atg gag tat agg cag tgt      912
Ser Ala Cys Ser Pro Val Cys Pro Ala Gly Met Glu Tyr Arg Gln Cys
290                 295                 300 gtg tcc cct tgc gcc agg acc tgc cag agc ctg cac atc aat gaa atg      960
Val Ser Pro Cys Ala Arg Thr Cys Gln Ser Leu His Ile Asn Glu Met
305                 310                 315                 320 tgt cag gag cga tgc gtg gat ggc tgc agc tgc cct gag gga cag ctc     1008
Cys Gln Glu Arg Cys Val Asp Gly Cys Ser Cys Pro Glu Gly Gln Leu
                325                 330                 335 ctg gat gaa ggc ctc tgc gtg gag agc acc gag tgt ccc tgc gtg cat     1056
Leu Asp Glu Gly Leu Cys Val Glu Ser Thr Glu Cys Pro Cys Val His
                340                 345                 350 tcc gga aag cgc tac cct ccc ggc acc tcc ctc tct cga gac tgc aac     1104
Ser Gly Lys Arg Tyr Pro Pro Gly Thr Ser Leu Ser Arg Asp Cys Asn
        355                 360                 365 acc tgc att tgc cga aac agc cag tgg atc tgc agc aat gaa gaa tgt     1152
Thr Cys Ile Cys Arg Asn Ser Gln Trp Ile Cys Ser Asn Glu Glu Cys
370                 375                 380 cca ggg gag tgc ctt gtc aca ggt caa tca cac ttc aag agc ttt gac     1200
Pro Gly Glu Cys Leu Val Thr Gly Gln Ser His Phe Lys Ser Phe Asp
385                 390                 395                 400 aac aga tac ttc acc ttc agt ggg atc tgc cag tac ctg ctg gcc cgg     1248
Asn Arg Tyr Phe Thr Phe Ser Gly Ile Cys Gln Tyr Leu Leu Ala Arg
                405                 410                 415 gat tgc cag gac cac tcc ttc tcc att gtc att gag act gtc cag tgt     1296
Asp Cys Gln Asp His Ser Phe Ser Ile Val Ile Glu Thr Val Gln Cys
                420                 425                 430 gct gat gac cgc gac gct gtg tgc acc cgc tcc gtc acc gtc cgg ctg     1344
Ala Asp Asp Arg Asp Ala Val Cys Thr Arg Ser Val Thr Val Arg Leu
        435                 440                 445 cct ggc ctg cac aac agc ctt gtg aaa ctg aag cat ggg gca gga gtt     1392
Pro Gly Leu His Asn Ser Leu Val Lys Leu Lys His Gly Ala Gly Val
450                 455                 460 gcc atg gat ggc cag gac gtc cag ctc ccc ctc ctg aaa ggt gac ctc     1440
Ala Met Asp Gly Gln Asp Val Gln Leu Pro Leu Leu Lys Gly Asp Leu
465                 470                 475                 480 cgc atc cag cat aca gtg acg gcc tcc gtg cgc ctc agc tac ggg gag     1488
Arg Ile Gln His Thr Val Thr Ala Ser Val Arg Leu Ser Tyr Gly Glu
                485                 490                 495 gac ctg cag atg gac tgg gat ggc cgc ggg agg ctg ctg gtg aag ctg     1536
```

```
                Asp Leu Gln Met Asp Trp Asp Gly Arg Gly Arg Leu Leu Val Lys Leu
                            500                 505                 510 tcc ccc gtc tat gcc ggg aag acc tgc ggc ctg tgt ggg aat tac aat      1584
Ser Pro Val Tyr Ala Gly Lys Thr Cys Gly Leu Cys Gly Asn Tyr Asn
            515                 520                 525 ggc aac cag ggc gac gac ttc ctt acc ccc tct ggg ctg gcg gag ccc      1632
Gly Asn Gln Gly Asp Asp Phe Leu Thr Pro Ser Gly Leu Ala Glu Pro
        530                 535                 540 cgg gtg gag gac ttc ggg aac gcc tgg aag ctg cac ggg gac tgc cag      1680
Arg Val Glu Asp Phe Gly Asn Ala Trp Lys Leu His Gly Asp Cys Gln
545                 550                 555                 560 gac ctg cag aag cag cac agc gat ccc tgc gcc ctc aac ccg cgc atg      1728
Asp Leu Gln Lys Gln His Ser Asp Pro Cys Ala Leu Asn Pro Arg Met
                565                 570                 575 acc agg ttc tcc gag gag gcg tgc gcg gtc ctg acg tcc ccc aca ttc      1776
Thr Arg Phe Ser Glu Glu Ala Cys Ala Val Leu Thr Ser Pro Thr Phe
            580                 585                 590 gag gcc tgc cat cgt gcc gtc agc ccg ctg ccc tac ctg cgg aac tgc      1824
Glu Ala Cys His Arg Ala Val Ser Pro Leu Pro Tyr Leu Arg Asn Cys
        595                 600                 605 cgc tac gac gtg tgc tcc tgc tcg gac ggc cgc gag tgc ctg tgc ggc      1872
Arg Tyr Asp Val Cys Ser Cys Ser Asp Gly Arg Glu Cys Leu Cys Gly
610                 615                 620 gcc ctg gcc agc tat gcc gcg gcc tgc gcg ggg aga ggc gtg cgc gtc      1920
Ala Leu Ala Ser Tyr Ala Ala Ala Cys Ala Gly Arg Gly Val Arg Val
625                 630                 635                 640 gcg tgg cgc gag cca ggc cgc tgt gag ctg aac tgc ccg aaa ggc cag      1968
Ala Trp Arg Glu Pro Gly Arg Cys Glu Leu Asn Cys Pro Lys Gly Gln
                645                 650                 655 gtg tac ctg cag tgc ggg acc ccc tgc aac ctg acc tgc cgc tct ctc      2016
Val Tyr Leu Gln Cys Gly Thr Pro Cys Asn Leu Thr Cys Arg Ser Leu
            660                 665                 670 tct tac ccg gat gag gaa tgc aat gag gcc tgc ctg gag ggc tgc ttc      2064
Ser Tyr Pro Asp Glu Glu Cys Asn Glu Ala Cys Leu Glu Gly Cys Phe
        675                 680                 685 tgc ccc cca ggg ctc tac atg gat gag agg ggg gac tgc gtg ccc aag      2112
Cys Pro Pro Gly Leu Tyr Met Asp Glu Arg Gly Asp Cys Val Pro Lys
690                 695                 700 gcc cag tgc ccc tgt tac tat gac ggt gag atc ttc cag cca gaa gac      2160
Ala Gln Cys Pro Cys Tyr Tyr Asp Gly Glu Ile Phe Gln Pro Glu Asp
705                 710                 715                 720 atc ttc tca gac cat cac acc atg tgc tac tgt gag gat ggc ttc atg      2208
Ile Phe Ser Asp His His Thr Met Cys Tyr Cys Glu Asp Gly Phe Met
                725                 730                 735 cac tgt acc atg agt gga gtc ccc gga agc ttg ctg cct gac gct gtc      2256
His Cys Thr Met Ser Gly Val Pro Gly Ser Leu Leu Pro Asp Ala Val
            740                 745                 750 ctc agc agt ccc ctg tct cat cgc agc aaa agg agc cta tcc tgt cgg      2304
Leu Ser Ser Pro Leu Ser His Arg Ser Lys Arg Ser Leu Ser Cys Arg
        755                 760                 765 ccc ccc atg gtc aag ctg gtg tgt ccc gct gac aac ctg cgg gct gaa      2352
Pro Pro Met Val Lys Leu Val Cys Pro Ala Asp Asn Leu Arg Ala Glu
770                 775                 780 ggg ctc gag tgt acc aaa acg tgc cag aac tat gac ctg gag tgc atg      2400
Gly Leu Glu Cys Thr Lys Thr Cys Gln Asn Tyr Asp Leu Glu Cys Met
785                 790                 795                 800 agc atg ggc tgt gtc tct ggc tgc ctc tgc ccc ccg ggc atg gtc cgg      2448
Ser Met Gly Cys Val Ser Gly Cys Leu Cys Pro Pro Gly Met Val Arg
                805                 810                 815
```

| | | |
|---|---|---|
| cat gag aac aga tgt gtg gcc ctg gaa agg tgt ccc tgc ttc cat cag<br>His Glu Asn Arg Cys Val Ala Leu Glu Arg Cys Pro Cys Phe His Gln<br>820        825            830 | | 2496 |
| ggc aag gag tat gcc cct gga gaa aca gtg aag att ggc tgc aac act<br>Gly Lys Glu Tyr Ala Pro Gly Glu Thr Val Lys Ile Gly Cys Asn Thr<br>835           840           845 | | 2544 |
| tgt gtc tgt cgg gac cgg aag tgg aac tgc aca gac cat gtg tgt gat<br>Cys Val Cys Arg Asp Arg Lys Trp Asn Cys Thr Asp His Val Cys Asp<br>850           855           860 | | 2592 |
| gcc acg tgc tcc acg atc ggc atg gcc cac tac ctc acc ttc gac ggg<br>Ala Thr Cys Ser Thr Ile Gly Met Ala His Tyr Leu Thr Phe Asp Gly<br>865           870           875           880 | | 2640 |
| ctc aaa tac ctg ttc ccc ggg gag tgc cag tac gtt ctg gtg cag gat<br>Leu Lys Tyr Leu Phe Pro Gly Glu Cys Gln Tyr Val Leu Val Gln Asp<br>            885           890           895 | | 2688 |
| tac tgc ggc agt aac cct ggg acc ttt cgg atc cta gtg ggg aat aag<br>Tyr Cys Gly Ser Asn Pro Gly Thr Phe Arg Ile Leu Val Gly Asn Lys<br>        900           905           910 | | 2736 |
| gga tgc agc cac ccc tca gtg aaa tgc aag aaa cgg gtc acc atc ctg<br>Gly Cys Ser His Pro Ser Val Lys Cys Lys Lys Arg Val Thr Ile Leu<br>        915           920           925 | | 2784 |
| gtg gag gga gga gag att gag ctg ttt gac ggg gag gtg aat gtg aag<br>Val Glu Gly Gly Glu Ile Glu Leu Phe Asp Gly Glu Val Asn Val Lys<br>930           935           940 | | 2832 |
| agg ccc atg aag gat gag act cac ttt gag gtg gtg gag tct ggc cgg<br>Arg Pro Met Lys Asp Glu Thr His Phe Glu Val Val Glu Ser Gly Arg<br>945           950           955           960 | | 2880 |
| tac atc att ctg ctg ctg ggc aaa gcc ctc tcc gtg gtc tgg gac cgc<br>Tyr Ile Ile Leu Leu Leu Gly Lys Ala Leu Ser Val Val Trp Asp Arg<br>            965           970           975 | | 2928 |
| cac ctg agc atc tcc gtg gtc ctg aag cag aca tac cag gag aaa gtg<br>His Leu Ser Ile Ser Val Val Leu Lys Gln Thr Tyr Gln Glu Lys Val<br>        980           985           990 | | 2976 |
| tgt ggc ctg tgt ggg aat ttt gat  ggc atc cag aac aat  gac ctc acc<br>Cys Gly Leu Cys Gly Asn Phe Asp  Gly Ile Gln Asn Asn  Asp Leu Thr<br>        995           1000           1005 | | 3024 |
| agc agc  aac ctc caa gtg gag  gaa gac cct gtg gac  ttt ggg aac<br>Ser Ser  Asn Leu Gln Val Glu  Glu Asp Pro Val Asp  Phe Gly Asn<br>1010           1015           1020 | | 3069 |
| tcc tgg  aaa gtg agc tcg cag  tgt gct gac acc aga  aaa gtg cct<br>Ser Trp  Lys Val Ser Ser Gln  Cys Ala Asp Thr Arg  Lys Val Pro<br>1025           1030           1035 | | 3114 |
| ctg gac  tca tcc cct gcc acc  tgc cat aac aac atc  atg aag cag<br>Leu Asp  Ser Ser Pro Ala Thr  Cys His Asn Asn Ile  Met Lys Gln<br>1040           1045           1050 | | 3159 |
| acg atg  gtg gat tcc tcc tgt  aga atc ctt acc agt  gac gtc ttc<br>Thr Met  Val Asp Ser Ser Cys  Arg Ile Leu Thr Ser  Asp Val Phe<br>1055           1060           1065 | | 3204 |
| cag gac  tgc aac aag ctg gtg  gac ccc gag cca tat  ctg gat gtc<br>Gln Asp  Cys Asn Lys Leu Val  Asp Pro Glu Pro Tyr  Leu Asp Val<br>1070           1075           1080 | | 3249 |
| tgc att  tac gac acc tgc tcc  tgt gag tcc att ggg  gac tgc gcc<br>Cys Ile  Tyr Asp Thr Cys Ser  Cys Glu Ser Ile Gly  Asp Cys Ala<br>1085           1090           1095 | | 3294 |
| tgc ttc  tgc gac acc att gct  gcc tat gcc cac gtg  tgt gcc cag<br>Cys Phe  Cys Asp Thr Ile Ala  Ala Tyr Ala His Val  Cys Ala Gln<br>1100           1105           1110 | | 3339 |
| cat ggc  aag gtg gtg acc tgg  agg acg gcc aca ttg  tgc ccc cag<br>His Gly  Lys Val Val Thr Trp  Arg Thr Ala Thr Leu  Cys Pro Gln<br>1115           1120           1125 | | 3384 |

```
agc tgc gag gag agg aat ctc cgg gag aac ggg tat gag tgt gag      3429
Ser Cys Glu Glu Arg Asn Leu Arg Glu Asn Gly Tyr Glu Cys Glu
    1130                1135                1140 tgg cgc tat aac agc tgt gca cct gcc tgt caa gtc acg tgt cag      3474
Trp Arg Tyr Asn Ser Cys Ala Pro Ala Cys Gln Val Thr Cys Gln
1145                1150                1155 cac cct gag cca ctg gcc tgc cct gtg cag tgt gtg gag ggc tgc      3519
His Pro Glu Pro Leu Ala Cys Pro Val Gln Cys Val Glu Gly Cys
        1160                1165                1170 cat gcc cac tgc cct cca ggg aaa atc ctg gat gag ctt ttg cag      3564
His Ala His Cys Pro Pro Gly Lys Ile Leu Asp Glu Leu Leu Gln
            1175                1180                1185 acc tgc gtt gac cct gaa gac tgt cca gtg tgt gag gtg gct ggc      3609
Thr Cys Val Asp Pro Glu Asp Cys Pro Val Cys Glu Val Ala Gly
    1190                1195                1200 cgg cgt ttt gcc tca gga aag aaa gtc acc ttg aat ccc agt gac      3654
Arg Arg Phe Ala Ser Gly Lys Lys Val Thr Leu Asn Pro Ser Asp
1205                1210                1215 cct gag cac tgc cag att tgc cac tgt gat gtt gtc aac ctc acc      3699
Pro Glu His Cys Gln Ile Cys His Cys Asp Val Val Asn Leu Thr
        1220                1225                1230 tgt gaa gcc tgc cag gag ccg gga ggc ctg gtg gtg cct ccc aca      3744
Cys Glu Ala Cys Gln Glu Pro Gly Gly Leu Val Val Pro Pro Thr
            1235                1240                1245 gat gcc ccg gtg agc ccc acc act ctg tat gtg gag gac atc tcg      3789
Asp Ala Pro Val Ser Pro Thr Thr Leu Tyr Val Glu Asp Ile Ser
    1250                1255                1260 gaa ccg ccg ttg cac gat ttc tac tgc agc agg cta ctg gac ctg      3834
Glu Pro Pro Leu His Asp Phe Tyr Cys Ser Arg Leu Leu Asp Leu
1265                1270                1275 gtc ttc ctg ctg gat ggc tcc tcc agg ctg tcc gag gct gag ttt      3879
Val Phe Leu Leu Asp Gly Ser Ser Arg Leu Ser Glu Ala Glu Phe
        1280                1285                1290 gaa gtg ctg aag gcc ttt gtg gtg gac atg atg gag cgg ctg cgc      3924
Glu Val Leu Lys Ala Phe Val Val Asp Met Met Glu Arg Leu Arg
            1295                1300                1305 atc tcc cag aag tgg gtc cgc gtg gcc gtg gtg gag tac cac gac      3969
Ile Ser Gln Lys Trp Val Arg Val Ala Val Val Glu Tyr His Asp
    1310                1315                1320 ggc tcc cac gcc tac atc ggg ctc aag gac cgg aag cga ccg tca      4014
Gly Ser His Ala Tyr Ile Gly Leu Lys Asp Arg Lys Arg Pro Ser
1325                1330                1335 gag ctg cgg cgc att gcc agc cag gtg aag tat gcg ggc agc cag      4059
Glu Leu Arg Arg Ile Ala Ser Gln Val Lys Tyr Ala Gly Ser Gln
        1340                1345                1350 gtg gcc tcc acc agc gag gtc ttg aaa tac aca ctg ttc caa atc      4104
Val Ala Ser Thr Ser Glu Val Leu Lys Tyr Thr Leu Phe Gln Ile
            1355                1360                1365 ttc agc aag atc gac cgc cct gaa gcc tcc cgc atc gcc ctg ctc      4149
Phe Ser Lys Ile Asp Arg Pro Glu Ala Ser Arg Ile Ala Leu Leu
    1370                1375                1380 ctg atg gcc agc cag gag ccc caa cgg atg tcc cgg aac ttt gtc      4194
Leu Met Ala Ser Gln Glu Pro Gln Arg Met Ser Arg Asn Phe Val
1385                1390                1395 cgc tac gtc cag ggc ctg aag aag aag aag gtc att gtg atc ccg      4239
Arg Tyr Val Gln Gly Leu Lys Lys Lys Lys Val Ile Val Ile Pro
        1400                1405                1410 gtg ggc att ggg ccc cat gcc aac ctc aag cag atc cgc ctc atc      4284
Val Gly Ile Gly Pro His Ala Asn Leu Lys Gln Ile Arg Leu Ile
```

-continued

|  |  |  |  |  |
|---|---|---|---|---|
| 1415 | | 1420 | | 1425 |

| gag aag cag gcc cct gag aac aag gcc ttc gtg ctg agc agt gtg | 4329 |
|---|---|
| Glu Lys Gln Ala Pro Glu Asn Lys Ala Phe Val Leu Ser Ser Val | |
| 1430                                          1435                                         1440 | |

```
gag aag cag gcc cct gag aac aag gcc ttc gtg ctg agc agt gtg       4329
Glu Lys Gln Ala Pro Glu Asn Lys Ala Phe Val Leu Ser Ser Val
        1430                1435                1440 gat gag ctg gag cag caa agg gac gag atc gtt agc tac ctc tgt       4374
Asp Glu Leu Glu Gln Gln Arg Asp Glu Ile Val Ser Tyr Leu Cys
        1445                1450                1455 gac ctt gcc cct gaa gcc cct cct cct act ctg ccc ccc cac atg       4419
Asp Leu Ala Pro Glu Ala Pro Pro Pro Thr Leu Pro Pro His Met
        1460                1465                1470 gca caa gtc act gtg ggc ccg ggg ctc ttg ggg gtt tcg acc ctg       4464
Ala Gln Val Thr Val Gly Pro Gly Leu Leu Gly Val Ser Thr Leu
        1475                1480                1485 ggg ccc aag agg aac tcc atg gtt ctg gat gtg gcg ttc gtc ctg       4509
Gly Pro Lys Arg Asn Ser Met Val Leu Asp Val Ala Phe Val Leu
        1490                1495                1500 gaa gga tcg gac aaa att ggt gaa gcc gac ttc aac agg agc aag       4554
Glu Gly Ser Asp Lys Ile Gly Glu Ala Asp Phe Asn Arg Ser Lys
        1505                1510                1515 gag ttc atg gag gag gtg att cag cgg atg gat gtg ggc cag gac       4599
Glu Phe Met Glu Glu Val Ile Gln Arg Met Asp Val Gly Gln Asp
        1520                1525                1530 agc atc cac gtc acg gtg ctg cag tac tcc tac atg gtg acc gtg       4644
Ser Ile His Val Thr Val Leu Gln Tyr Ser Tyr Met Val Thr Val
        1535                1540                1545 gag tac ccc ttc agc gag gca cag tcc aaa ggg gac atc ctg cag       4689
Glu Tyr Pro Phe Ser Glu Ala Gln Ser Lys Gly Asp Ile Leu Gln
        1550                1555                1560 cgg gtg cga gag atc cgc tac cag ggc ggc aac agg acc aac act       4734
Arg Val Arg Glu Ile Arg Tyr Gln Gly Gly Asn Arg Thr Asn Thr
        1565                1570                1575 ggg ctg gcc ctg cgg tac ctc tct gac cac agc ttc ttg gtc agc       4779
Gly Leu Ala Leu Arg Tyr Leu Ser Asp His Ser Phe Leu Val Ser
        1580                1585                1590 cag ggt gac cgg gag cag gcg ccc aac ctg gtc tac atg gtc acc       4824
Gln Gly Asp Arg Glu Gln Ala Pro Asn Leu Val Tyr Met Val Thr
        1595                1600                1605 gga aat cct gcc tct gat gag atc aag agg ctg cct gga gac atc       4869
Gly Asn Pro Ala Ser Asp Glu Ile Lys Arg Leu Pro Gly Asp Ile
        1610                1615                1620 cag gtg gtg ccc att gga gtg ggc cct aat gcc aac gtg cag gag       4914
Gln Val Val Pro Ile Gly Val Gly Pro Asn Ala Asn Val Gln Glu
        1625                1630                1635 ctg gag agg att ggc tgg ccc aat gcc cct atc ctc atc cag gac       4959
Leu Glu Arg Ile Gly Trp Pro Asn Ala Pro Ile Leu Ile Gln Asp
        1640                1645                1650 ttt gag acg ctc ccc cga gag gct cct gac ctg gtg ctg cag agg       5004
Phe Glu Thr Leu Pro Arg Glu Ala Pro Asp Leu Val Leu Gln Arg
        1655                1660                1665 tgc tgc tcc gga gag ggg ctg cag atc ccc acc ctc tcc cct gca       5049
Cys Cys Ser Gly Glu Gly Leu Gln Ile Pro Thr Leu Ser Pro Ala
        1670                1675                1680 cct gac tgc agc cag ccc ctg gac gtg atc ctt ctc ctg gat ggc       5094
Pro Asp Cys Ser Gln Pro Leu Asp Val Ile Leu Leu Leu Asp Gly
        1685                1690                1695 tcc tcc agt ttc cca gct tct tat ttt gat gaa atg aag agt ttc       5139
Ser Ser Ser Phe Pro Ala Ser Tyr Phe Asp Glu Met Lys Ser Phe
        1700                1705                1710 gcc aag gct ttc att tca aaa gcc aat ata ggg cct cgt ctc act       5184
```

-continued

| | | | | | | | | | | | | | | |
|---|---|---|---|---|---|---|---|---|---|---|---|---|---|---|
| Ala | Lys | Ala | Phe | Ile | Ser | Lys | Ala | Asn | Ile | Gly | Pro | Arg | Leu | Thr |
| | 1715 | | | | 1720 | | | | | 1725 | | | | |

```
cag gtg tca gtg ctg cag tat gga agc atc acc acc att gac gtg    5229
Gln Val Ser Val Leu Gln Tyr Gly Ser Ile Thr Thr Ile Asp Val
    1730            1735                1740 cca tgg aac gtg gtc ccg gag aaa gcc cat ttg ctg agc ctt gtg    5274
Pro Trp Asn Val Val Pro Glu Lys Ala His Leu Leu Ser Leu Val
    1745            1750                1755 gac gtc atg cag cgg gag gga ggc ccc agc caa atc ggg gat gcc    5319
Asp Val Met Gln Arg Glu Gly Gly Pro Ser Gln Ile Gly Asp Ala
    1760            1765                1770 ttg ggc ttt gct gtg cga tac ttg act tca gaa atg cat ggg gcg    5364
Leu Gly Phe Ala Val Arg Tyr Leu Thr Ser Glu Met His Gly Ala
    1775            1780                1785 cgc ccg gga gcc tca aag gcg gtg gtc atc ctg gtc acg gac gtc    5409
Arg Pro Gly Ala Ser Lys Ala Val Val Ile Leu Val Thr Asp Val
    1790            1795                1800 tct gtg gat tca gtg gat gca gca gct gat gcc gcc agg tcc aac    5454
Ser Val Asp Ser Val Asp Ala Ala Ala Asp Ala Ala Arg Ser Asn
    1805            1810                1815 aga gtg aca gtg ttc cct att gga att gga gat cgc tac gat gca    5499
Arg Val Thr Val Phe Pro Ile Gly Ile Gly Asp Arg Tyr Asp Ala
    1820            1825                1830 gcc cag cta cgg atc ttg gca ggc cca gca ggc gac tcc aac gtg    5544
Ala Gln Leu Arg Ile Leu Ala Gly Pro Ala Gly Asp Ser Asn Val
    1835            1840                1845 gtg aag ctc cag cga atc gaa gac ctc cct acc atg gtc acc ttg    5589
Val Lys Leu Gln Arg Ile Glu Asp Leu Pro Thr Met Val Thr Leu
    1850            1855                1860 ggc aat tcc ttc ctc cac aaa ctg tgc tct gga ttt gtt agg att    5634
Gly Asn Ser Phe Leu His Lys Leu Cys Ser Gly Phe Val Arg Ile
    1865            1870                1875 tgc atg gat gag gat ggg aat gag aag agg ccc ggg gac gtc tgg    5679
Cys Met Asp Glu Asp Gly Asn Glu Lys Arg Pro Gly Asp Val Trp
    1880            1885                1890 acc ttg cca gac cag tgc cac acc gtg act tgc cag cca gat ggc    5724
Thr Leu Pro Asp Gln Cys His Thr Val Thr Cys Gln Pro Asp Gly
    1895            1900                1905 cag acc ttg ctg aag agt cat cgg gtc aac tgt gac cgg ggg ctg    5769
Gln Thr Leu Leu Lys Ser His Arg Val Asn Cys Asp Arg Gly Leu
    1910            1915                1920 agg cct tcg tgc cct aac agc cag tcc cct gtt aaa gtg gaa gag    5814
Arg Pro Ser Cys Pro Asn Ser Gln Ser Pro Val Lys Val Glu Glu
    1925            1930                1935 acc tgt ggc tgc cgc tgg acc tgc ccc tgc gtg tgc aca ggc agc    5859
Thr Cys Gly Cys Arg Trp Thr Cys Pro Cys Val Cys Thr Gly Ser
    1940            1945                1950 tcc act cgg cac atc gtg acc ttt gat ggg cag aat ttc aag ctg    5904
Ser Thr Arg His Ile Val Thr Phe Asp Gly Gln Asn Phe Lys Leu
    1955            1960                1965 act ggc agc tgt tct tat gtc cta ttt caa aac aag gag cag gac    5949
Thr Gly Ser Cys Ser Tyr Val Leu Phe Gln Asn Lys Glu Gln Asp
    1970            1975                1980 ctg gag gtg att ctc cat aat ggt gcc tgc agc cct gga gca agg    5994
Leu Glu Val Ile Leu His Asn Gly Ala Cys Ser Pro Gly Ala Arg
    1985            1990                1995 cag ggc tgc atg aaa tcc atc gag gtg aag cac agt gcc ctc tcc    6039
Gln Gly Cys Met Lys Ser Ile Glu Val Lys His Ser Ala Leu Ser
    2000            2005                2010
```

| | | | | | | | | | | | | | | |
|---|---|---|---|---|---|---|---|---|---|---|---|---|---|---|
| gtc | gag | ctg | cac | agt | gac | atg | gag | gtg | acg | gtg | aat | ggg | aga | ctg | 6084 |
| Val | Glu | Leu | His | Ser | Asp | Met | Glu | Val | Thr | Val | Asn | Gly | Arg | Leu | |
| | | | | 2015 | | | | 2020 | | | | 2025 | | | |
| gtc | tct | gtt | cct | tac | gtg | ggt | ggg | aac | atg | gaa | gtc | aac | gtt | tat | 6129 |
| Val | Ser | Val | Pro | Tyr | Val | Gly | Gly | Asn | Met | Glu | Val | Asn | Val | Tyr | |
| | | | | 2030 | | | | 2035 | | | | 2040 | | | |
| ggt | gcc | atc | atg | cat | gag | gtc | aga | ttc | aat | cac | ctt | ggt | cac | atc | 6174 |
| Gly | Ala | Ile | Met | His | Glu | Val | Arg | Phe | Asn | His | Leu | Gly | His | Ile | |
| | | | | 2045 | | | | 2050 | | | | 2055 | | | |
| ttc | aca | ttc | act | cca | caa | aac | aat | gag | ttc | caa | ctg | cag | ctc | agc | 6219 |
| Phe | Thr | Phe | Thr | Pro | Gln | Asn | Asn | Glu | Phe | Gln | Leu | Gln | Leu | Ser | |
| | | | | 2060 | | | | 2065 | | | | 2070 | | | |
| ccc | aag | act | ttt | gct | tca | aag | acg | tat | ggt | ctg | tgt | ggg | atc | tgt | 6264 |
| Pro | Lys | Thr | Phe | Ala | Ser | Lys | Thr | Tyr | Gly | Leu | Cys | Gly | Ile | Cys | |
| | | | | 2075 | | | | 2080 | | | | 2085 | | | |
| gat | gag | aac | gga | gcc | aat | gac | ttc | atg | ctg | agg | gat | ggc | aca | gtc | 6309 |
| Asp | Glu | Asn | Gly | Ala | Asn | Asp | Phe | Met | Leu | Arg | Asp | Gly | Thr | Val | |
| | | | | 2090 | | | | 2095 | | | | 2100 | | | |
| acc | aca | gac | tgg | aaa | aca | ctt | gtt | cag | gaa | tgg | act | gtg | cag | cgg | 6354 |
| Thr | Thr | Asp | Trp | Lys | Thr | Leu | Val | Gln | Glu | Trp | Thr | Val | Gln | Arg | |
| | | | | 2105 | | | | 2110 | | | | 2115 | | | |
| cca | ggg | cag | acg | tgc | cag | ccc | atc | ctg | gag | gag | cag | tgt | ctt | gtc | 6399 |
| Pro | Gly | Gln | Thr | Cys | Gln | Pro | Ile | Leu | Glu | Glu | Gln | Cys | Leu | Val | |
| | | | | 2120 | | | | 2125 | | | | 2130 | | | |
| ccc | gac | agc | tcc | cac | tgc | cag | gtc | ctc | ctc | tta | cca | ctg | ttt | gct | 6444 |
| Pro | Asp | Ser | Ser | His | Cys | Gln | Val | Leu | Leu | Leu | Pro | Leu | Phe | Ala | |
| | | | | 2135 | | | | 2140 | | | | 2145 | | | |
| gaa | tgc | cac | aag | gtc | ctg | gct | cca | gcc | aca | ttc | tat | gcc | atc | tgc | 6489 |
| Glu | Cys | His | Lys | Val | Leu | Ala | Pro | Ala | Thr | Phe | Tyr | Ala | Ile | Cys | |
| | | | | 2150 | | | | 2155 | | | | 2160 | | | |
| cag | cag | gac | agt | tgc | cac | cag | gag | caa | gtg | tgt | gag | gtg | atc | gcc | 6534 |
| Gln | Gln | Asp | Ser | Cys | His | Gln | Glu | Gln | Val | Cys | Glu | Val | Ile | Ala | |
| | | | | 2165 | | | | 2170 | | | | 2175 | | | |
| tct | tat | gcc | cac | ctc | tgt | cgg | acc | aac | ggg | gtc | tgc | gtt | gac | tgg | 6579 |
| Ser | Tyr | Ala | His | Leu | Cys | Arg | Thr | Asn | Gly | Val | Cys | Val | Asp | Trp | |
| | | | | 2180 | | | | 2185 | | | | 2190 | | | |
| agg | aca | cct | gat | ttc | tgt | gct | atg | tca | tgc | cca | cca | tct | ctg | gtt | 6624 |
| Arg | Thr | Pro | Asp | Phe | Cys | Ala | Met | Ser | Cys | Pro | Pro | Ser | Leu | Val | |
| | | | | 2195 | | | | 2200 | | | | 2205 | | | |
| tat | aac | cac | tgt | gag | cat | ggc | tgt | ccc | cgg | cac | tgt | gat | ggc | aac | 6669 |
| Tyr | Asn | His | Cys | Glu | His | Gly | Cys | Pro | Arg | His | Cys | Asp | Gly | Asn | |
| | | | | 2210 | | | | 2215 | | | | 2220 | | | |
| gtg | agc | tcc | tgt | ggg | gac | cat | ccc | tcc | gaa | ggc | tgt | ttc | tgc | cct | 6714 |
| Val | Ser | Ser | Cys | Gly | Asp | His | Pro | Ser | Glu | Gly | Cys | Phe | Cys | Pro | |
| | | | | 2225 | | | | 2230 | | | | 2235 | | | |
| cca | gat | aaa | gtc | atg | ttg | gaa | ggc | agc | tgt | gtc | cct | gaa | gag | gcc | 6759 |
| Pro | Asp | Lys | Val | Met | Leu | Glu | Gly | Ser | Cys | Val | Pro | Glu | Glu | Ala | |
| | | | | 2240 | | | | 2245 | | | | 2250 | | | |
| tgc | act | cag | tgc | att | ggt | gag | gat | gga | gtc | cag | cac | cag | ttc | ctg | 6804 |
| Cys | Thr | Gln | Cys | Ile | Gly | Glu | Asp | Gly | Val | Gln | His | Gln | Phe | Leu | |
| | | | | 2255 | | | | 2260 | | | | 2265 | | | |
| gaa | gcc | tgg | gtc | ccg | gac | cac | cag | ccc | tgt | cag | atc | tgc | aca | tgc | 6849 |
| Glu | Ala | Trp | Val | Pro | Asp | His | Gln | Pro | Cys | Gln | Ile | Cys | Thr | Cys | |
| | | | | 2270 | | | | 2275 | | | | 2280 | | | |
| ctc | agc | ggg | cgg | aag | gtc | aac | tgc | aca | acg | cag | ccc | tgc | ccc | acg | 6894 |
| Leu | Ser | Gly | Arg | Lys | Val | Asn | Cys | Thr | Thr | Gln | Pro | Cys | Pro | Thr | |
| | | | | 2285 | | | | 2290 | | | | 2295 | | | |
| gcc | aaa | gct | ccc | acg | tgt | ggc | ctg | tgt | gaa | gta | gcc | cgc | ctc | cgc | 6939 |
| Ala | Lys | Ala | Pro | Thr | Cys | Gly | Leu | Cys | Glu | Val | Ala | Arg | Leu | Arg | |
| | | | | 2300 | | | | 2305 | | | | 2310 | | | |

-continued

```
cag aat gca gac cag tgc tgc ccc gag tat gag tgt gtg tgt gac        6984
Gln Asn Ala Asp Gln Cys Cys Pro Glu Tyr Glu Cys Val Cys Asp
    2315                2320                2325 cca gtg agc tgt gac ctg ccc cca gtg cct cac tgt gaa cgt ggc        7029
Pro Val Ser Cys Asp Leu Pro Pro Val Pro His Cys Glu Arg Gly
    2330                2335                2340 ctc cag ccc aca ctg acc aac cct ggc gag tgc aga ccc aac ttc        7074
Leu Gln Pro Thr Leu Thr Asn Pro Gly Glu Cys Arg Pro Asn Phe
    2345                2350                2355 acc tgc gcc tgc agg aag gag gag tgc aaa aga gtg tcc cca ccc        7119
Thr Cys Ala Cys Arg Lys Glu Glu Cys Lys Arg Val Ser Pro Pro
    2360                2365                2370 tcc tgc ccc ccg cac cgt ttg ccc acc ctt cgg aag acc cag tgc        7164
Ser Cys Pro Pro His Arg Leu Pro Thr Leu Arg Lys Thr Gln Cys
    2375                2380                2385 tgt gat gag tat gag tgt gcc tgc aac tgt gtc aac tcc aca gtg        7209
Cys Asp Glu Tyr Glu Cys Ala Cys Asn Cys Val Asn Ser Thr Val
    2390                2395                2400 agc tgt ccc ctt ggg tac ttg gcc tca acc gcc acc aat gac tgt        7254
Ser Cys Pro Leu Gly Tyr Leu Ala Ser Thr Ala Thr Asn Asp Cys
    2405                2410                2415 ggc tgt acc aca acc acc tgc ctt ccc gac aag gtg tgt gtc cac        7299
Gly Cys Thr Thr Thr Thr Cys Leu Pro Asp Lys Val Cys Val His
    2420                2425                2430 cga agc acc atc tac cct gtg ggc cag ttc tgg gag gag ggc tgc        7344
Arg Ser Thr Ile Tyr Pro Val Gly Gln Phe Trp Glu Glu Gly Cys
    2435                2440                2445 gat gtg tgc acc tgc acc gac atg gag gat gcc gtg atg ggc ctc        7389
Asp Val Cys Thr Cys Thr Asp Met Glu Asp Ala Val Met Gly Leu
    2450                2455                2460 cgc gtg gcc cag tgc tcc cag aag ccc tgt gag gac agc tgt cgg        7434
Arg Val Ala Gln Cys Ser Gln Lys Pro Cys Glu Asp Ser Cys Arg
    2465                2470                2475 tcg ggc ttc act tac gtt ctc cat gaa ggc gag tgc tgt gga agg        7479
Ser Gly Phe Thr Tyr Val Leu His Glu Gly Glu Cys Cys Gly Arg
    2480                2485                2490 tgc ctg cca tct gcc tgt gag gtg gtg act ggc tca ccg cgg ggg        7524
Cys Leu Pro Ser Ala Cys Glu Val Val Thr Gly Ser Pro Arg Gly
    2495                2500                2505 gac tcc cag tct tcc tgg aag agt gtc ggc tcc cag tgg gcc tcc        7569
Asp Ser Gln Ser Ser Trp Lys Ser Val Gly Ser Gln Trp Ala Ser
    2510                2515                2520 ccg gag aac ccc tgc ctc atc aat gag tgt gtc cga gtg aag gag        7614
Pro Glu Asn Pro Cys Leu Ile Asn Glu Cys Val Arg Val Lys Glu
    2525                2530                2535 gag gtc ttt ata caa caa agg aac gtc tcc tgc ccc cag ctg gag        7659
Glu Val Phe Ile Gln Gln Arg Asn Val Ser Cys Pro Gln Leu Glu
    2540                2545                2550 gtc cct gtc tgc ccc tcg ggc ttt cag ctg agc tgt aag acc tca        7704
Val Pro Val Cys Pro Ser Gly Phe Gln Leu Ser Cys Lys Thr Ser
    2555                2560                2565 gcg tgc tgc cca agc tgt cgc tgt gag cgc atg gag gcc tgc atg        7749
Ala Cys Cys Pro Ser Cys Arg Cys Glu Arg Met Glu Ala Cys Met
    2570                2575                2580 ctc aat ggc act gtc att ggg ccc ggg aag act gtg atg atc gat        7794
Leu Asn Gly Thr Val Ile Gly Pro Gly Lys Thr Val Met Ile Asp
    2585                2590                2595 gtg tgc acg acc tgc cgc tgc atg gtg cag gtg ggg gtc atc tct        7839
Val Cys Thr Thr Cys Arg Cys Met Val Gln Val Gly Val Ile Ser
```

-continued

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     |     | 2600|     |     |     | 2605|     |     |     | 2610|     |     |      |
| gga | ttc | aag | ctg | gag | tgc | agg | aag | acc | acc | tgc | aac | ccc | tgc | ccc | 7884 |
| Gly | Phe | Lys | Leu | Glu | Cys | Arg | Lys | Thr | Thr | Cys | Asn | Pro | Cys | Pro |      |
|     | 2615|     |     |     | 2620|     |     |     | 2625|     |     |     |     |     |      |
| ctg | ggt | tac | aag | gaa | gaa | aat | aac | aca | ggt | gaa | tgt | tgt | ggg | aga | 7929 |
| Leu | Gly | Tyr | Lys | Glu | Glu | Asn | Asn | Thr | Gly | Glu | Cys | Cys | Gly | Arg |      |
|     | 2630|     |     |     | 2635|     |     |     | 2640|     |     |     |     |     |      |
| tgt | ttg | cct | acg | gct | tgc | acc | att | cag | cta | aga | gga | gga | cag | atc | 7974 |
| Cys | Leu | Pro | Thr | Ala | Cys | Thr | Ile | Gln | Leu | Arg | Gly | Gly | Gln | Ile |      |
|     | 2645|     |     |     | 2650|     |     |     | 2655|     |     |     |     |     |      |
| atg | aca | ctg | aag | cgt | gat | gag | acg | ctc | cag | gat | ggc | tgt | gat | act | 8019 |
| Met | Thr | Leu | Lys | Arg | Asp | Glu | Thr | Leu | Gln | Asp | Gly | Cys | Asp | Thr |      |
|     | 2660|     |     |     | 2665|     |     |     | 2670|     |     |     |     |     |      |
| cac | ttc | tgc | aag | gtc | aat | gag | aga | gga | gag | tac | ttc | tgg | gag | aag | 8064 |
| His | Phe | Cys | Lys | Val | Asn | Glu | Arg | Gly | Glu | Tyr | Phe | Trp | Glu | Lys |      |
|     | 2675|     |     |     | 2680|     |     |     | 2685|     |     |     |     |     |      |
| agg | gtc | aca | ggc | tgc | cca | ccc | ttt | gat | gaa | cac | aag | tgt | ctg | gct | 8109 |
| Arg | Val | Thr | Gly | Cys | Pro | Pro | Phe | Asp | Glu | His | Lys | Cys | Leu | Ala |      |
|     | 2690|     |     |     | 2695|     |     |     | 2700|     |     |     |     |     |      |
| gag | gga | ggt | aaa | att | atg | aaa | att | cca | ggc | acc | tgc | tgt | gac | aca | 8154 |
| Glu | Gly | Gly | Lys | Ile | Met | Lys | Ile | Pro | Gly | Thr | Cys | Cys | Asp | Thr |      |
|     | 2705|     |     |     | 2710|     |     |     | 2715|     |     |     |     |     |      |
| tgt | gag | gag | cct | gag | tgc | aac | gac | atc | act | gcc | agg | ctg | cag | tat | 8199 |
| Cys | Glu | Glu | Pro | Glu | Cys | Asn | Asp | Ile | Thr | Ala | Arg | Leu | Gln | Tyr |      |
|     | 2720|     |     |     | 2725|     |     |     | 2730|     |     |     |     |     |      |
| gtc | aag | gtg | gga | agc | tgt | aag | tct | gaa | gta | gag | gtg | gat | atc | cac | 8244 |
| Val | Lys | Val | Gly | Ser | Cys | Lys | Ser | Glu | Val | Glu | Val | Asp | Ile | His |      |
|     | 2735|     |     |     | 2740|     |     |     | 2745|     |     |     |     |     |      |
| tac | tgc | cag | ggc | aaa | tgt | gcc | agc | aaa | gcc | atg | tac | tcc | att | gac | 8289 |
| Tyr | Cys | Gln | Gly | Lys | Cys | Ala | Ser | Lys | Ala | Met | Tyr | Ser | Ile | Asp |      |
|     | 2750|     |     |     | 2755|     |     |     | 2760|     |     |     |     |     |      |
| atc | aac | gat | gtg | cag | gac | cag | tgc | tcc | tgc | tgc | tct | ccg | aca | cgg | 8334 |
| Ile | Asn | Asp | Val | Gln | Asp | Gln | Cys | Ser | Cys | Cys | Ser | Pro | Thr | Arg |      |
|     | 2765|     |     |     | 2770|     |     |     | 2775|     |     |     |     |     |      |
| acg | gag | ccc | atg | cag | gtg | gcc | ctg | cac | tgc | acc | aat | ggc | tct | gtt | 8379 |
| Thr | Glu | Pro | Met | Gln | Val | Ala | Leu | His | Cys | Thr | Asn | Gly | Ser | Val |      |
|     | 2780|     |     |     | 2785|     |     |     | 2790|     |     |     |     |     |      |
| gtg | tac | cat | gag | gtt | ctc | aat | gcc | atg | gag | tgc | aaa | tgc | tcc | ccc | 8424 |
| Val | Tyr | His | Glu | Val | Leu | Asn | Ala | Met | Glu | Cys | Lys | Cys | Ser | Pro |      |
|     | 2795|     |     |     | 2800|     |     |     | 2805|     |     |     |     |     |      |
| agg | aag | tgc | agc | aag | tga |     |     |     |     |     |     |     |     |     | 8442 |
| Arg | Lys | Cys | Ser | Lys |     |     |     |     |     |     |     |     |     |     |      |
|     | 2810|     |     |     |     |     |     |     |     |     |     |     |     |     |      |

<210> SEQ ID NO 2
<211> LENGTH: 2813
<212> TYPE: PRT
<213> ORGANISM: Homo sapiens

<400> SEQUENCE: 2

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys

```
                65                  70                  75                  80
Arg Val Ser Leu Ser Val Tyr Leu Gly Glu Phe Phe Asp Ile His Leu
                    85                  90                  95
Phe Val Asn Gly Thr Val Thr Gln Gly Asp Gln Arg Val Ser Met Pro
                    100                 105                 110
Tyr Ala Ser Lys Gly Leu Tyr Leu Glu Thr Glu Ala Gly Tyr Tyr Lys
                    115                 120                 125
Leu Ser Gly Glu Ala Tyr Gly Phe Val Ala Arg Ile Asp Gly Ser Gly
130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                    165                 170                 175
Glu Gly Thr Leu Thr Ser Asp Pro Tyr Asp Phe Ala Asn Ser Trp Ala
                    180                 185                 190
Leu Ser Ser Gly Glu Gln Trp Cys Glu Arg Ala Ser Pro Pro Ser Ser
                    195                 200                 205
Ser Cys Asn Ile Ser Ser Gly Glu Met Gln Lys Gly Leu Trp Glu Gln
                    210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                    245                 250                 255
Cys Ala Gly Gly Leu Glu Cys Ala Cys Pro Ala Leu Leu Glu Tyr Ala
                    260                 265                 270
Arg Thr Cys Ala Gln Glu Gly Met Val Leu Tyr Gly Trp Thr Asp His
                    275                 280                 285
Ser Ala Cys Ser Pro Val Cys Pro Ala Gly Met Glu Tyr Arg Gln Cys
                    290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                    325                 330                 335
Leu Asp Glu Gly Leu Cys Val Glu Ser Thr Glu Cys Pro Cys Val His
                    340                 345                 350
Ser Gly Lys Arg Tyr Pro Pro Gly Thr Ser Leu Ser Arg Asp Cys Asn
                    355                 360                 365
Thr Cys Ile Cys Arg Asn Ser Gln Trp Ile Cys Ser Asn Glu Glu Cys
                    370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                    405                 410                 415
Asp Cys Gln Asp His Ser Phe Ser Ile Val Ile Glu Thr Val Gln Cys
                    420                 425                 430
Ala Asp Asp Arg Asp Ala Val Cys Thr Arg Ser Val Thr Val Arg Leu
                    435                 440                 445
Pro Gly Leu His Asn Ser Leu Val Lys Leu Lys His Gly Ala Gly Val
                    450                 455                 460
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                    485                 490                 495
```

```
Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
        580                 585                 590

Glu Ala Cys His Arg Ala Val Ser Pro Leu Pro Tyr Leu Arg Asn Cys
    595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
        660                 665                 670

Ser Tyr Pro Asp Glu Glu Cys Asn Glu Ala Cys Leu Glu Gly Cys Phe
    675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
        740                 745                 750

Leu Ser Ser Pro Leu Ser His Arg Ser Lys Arg Ser Leu Ser Cys Arg
    755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
        820                 825                 830

Gly Lys Glu Tyr Ala Pro Gly Glu Thr Val Lys Ile Gly Cys Asn Thr
    835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
            885                 890                 895

Tyr Cys Gly Ser Asn Pro Gly Thr Phe Arg Ile Leu Val Gly Asn Lys
        900                 905                 910
```

-continued

```
Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
        930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn Asp Leu Thr
        995                 1000                1005

Ser Ser Asn Leu Gln Val Glu  Glu Asp Pro Val Asp  Phe Gly Asn
        1010                1015                1020

Ser Trp Lys Val Ser Ser Gln  Cys Ala Asp Thr Arg  Lys Val Pro
        1025                1030                1035

Leu Asp Ser Ser Pro Ala Thr  Cys His Asn Asn Ile  Met Lys Gln
        1040                1045                1050

Thr Met Val Asp Ser Ser Cys  Arg Ile Leu Thr Ser  Asp Val Phe
        1055                1060                1065

Gln Asp Cys Asn Lys Leu Val  Asp Pro Glu Pro Tyr  Leu Asp Val
        1070                1075                1080

Cys Ile Tyr Asp Thr Cys Ser  Cys Glu Ser Ile Gly  Asp Cys Ala
        1085                1090                1095

Cys Phe Cys Asp Thr Ile Ala  Ala Tyr Ala His Val  Cys Ala Gln
        1100                1105                1110

His Gly Lys Val Val Thr Trp  Arg Thr Ala Thr Leu  Cys Pro Gln
        1115                1120                1125

Ser Cys Glu Glu Arg Asn Leu  Arg Glu Asn Gly Tyr  Glu Cys Glu
        1130                1135                1140

Trp Arg Tyr Asn Ser Cys Ala  Pro Ala Cys Gln Val  Thr Cys Gln
        1145                1150                1155

His Pro Glu Pro Leu Ala Cys  Pro Val Gln Cys Val  Glu Gly Cys
        1160                1165                1170

His Ala His Cys Pro Pro Gly  Lys Ile Leu Asp Glu  Leu Leu Gln
        1175                1180                1185

Thr Cys Val Asp Pro Glu Asp  Cys Pro Val Cys Glu  Val Ala Gly
        1190                1195                1200

Arg Arg Phe Ala Ser Gly Lys  Lys Val Thr Leu Asn  Pro Ser Asp
        1205                1210                1215

Pro Glu His Cys Gln Ile Cys  His Cys Asp Val Val  Asn Leu Thr
        1220                1225                1230

Cys Glu Ala Cys Gln Glu Pro  Gly Gly Leu Val Val  Pro Pro Thr
        1235                1240                1245

Asp Ala Pro Val Ser Pro Thr  Thr Leu Tyr Val Glu  Asp Ile Ser
        1250                1255                1260

Glu Pro Pro Leu His Asp Phe  Tyr Cys Ser Arg Leu  Leu Asp Leu
        1265                1270                1275

Val Phe Leu Leu Asp Gly Ser  Ser Arg Leu Ser Glu  Ala Glu Phe
        1280                1285                1290

Glu Val Leu Lys Ala Phe Val  Val Asp Met Met Glu  Arg Leu Arg
        1295                1300                1305

Ile Ser Gln Lys Trp Val Arg  Val Ala Val Val Glu  Tyr His Asp
```

```
       1310                1315                1320

Gly Ser His Ala Tyr Ile Gly Leu Lys Asp Arg Lys Arg Pro Ser
       1325                1330                1335

Glu Leu Arg Arg Ile Ala Ser Gln Val Lys Tyr Ala Gly Ser Gln
       1340                1345                1350

Val Ala Ser Thr Ser Glu Val Leu Lys Tyr Thr Leu Phe Gln Ile
       1355                1360                1365

Phe Ser Lys Ile Asp Arg Pro Glu Ala Ser Arg Ile Ala Leu Leu
       1370                1375                1380

Leu Met Ala Ser Gln Glu Pro Gln Arg Met Ser Arg Asn Phe Val
       1385                1390                1395

Arg Tyr Val Gln Gly Leu Lys Lys Lys Val Ile Val Ile Pro
       1400                1405                1410

Val Gly Ile Gly Pro His Ala Asn Leu Lys Gln Ile Arg Leu Ile
       1415                1420                1425

Glu Lys Gln Ala Pro Glu Asn Lys Ala Phe Val Leu Ser Ser Val
       1430                1435                1440

Asp Glu Leu Glu Gln Gln Arg Asp Glu Ile Val Ser Tyr Leu Cys
       1445                1450                1455

Asp Leu Ala Pro Glu Ala Pro Pro Pro Thr Leu Pro Pro His Met
       1460                1465                1470

Ala Gln Val Thr Val Gly Pro Gly Leu Leu Gly Val Ser Thr Leu
       1475                1480                1485

Gly Pro Lys Arg Asn Ser Met Val Leu Asp Val Ala Phe Val Leu
       1490                1495                1500

Glu Gly Ser Asp Lys Ile Gly Glu Ala Asp Phe Asn Arg Ser Lys
       1505                1510                1515

Glu Phe Met Glu Glu Val Ile Gln Arg Met Asp Val Gly Gln Asp
       1520                1525                1530

Ser Ile His Val Thr Val Leu Gln Tyr Ser Tyr Met Val Thr Val
       1535                1540                1545

Glu Tyr Pro Phe Ser Glu Ala Gln Ser Lys Gly Asp Ile Leu Gln
       1550                1555                1560

Arg Val Arg Glu Ile Arg Tyr Gln Gly Gly Asn Arg Thr Asn Thr
       1565                1570                1575

Gly Leu Ala Leu Arg Tyr Leu Ser Asp His Ser Phe Leu Val Ser
       1580                1585                1590

Gln Gly Asp Arg Glu Gln Ala Pro Asn Leu Val Tyr Met Val Thr
       1595                1600                1605

Gly Asn Pro Ala Ser Asp Glu Ile Lys Arg Leu Pro Gly Asp Ile
       1610                1615                1620

Gln Val Val Pro Ile Gly Val Gly Pro Asn Ala Asn Val Gln Glu
       1625                1630                1635

Leu Glu Arg Ile Gly Trp Pro Asn Ala Pro Ile Leu Ile Gln Asp
       1640                1645                1650

Phe Glu Thr Leu Pro Arg Glu Ala Pro Asp Leu Val Leu Gln Arg
       1655                1660                1665

Cys Cys Ser Gly Glu Gly Leu Gln Ile Pro Thr Leu Ser Pro Ala
       1670                1675                1680

Pro Asp Cys Ser Gln Pro Leu Asp Val Ile Leu Leu Leu Asp Gly
       1685                1690                1695

Ser Ser Ser Phe Pro Ala Ser Tyr Phe Asp Glu Met Lys Ser Phe
       1700                1705                1710
```

```
Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
1760                1765                1770

Leu Gly Phe Ala Val Arg Tyr Leu Thr Ser Glu Met His Gly Ala
1775                1780                1785

Arg Pro Gly Ala Ser Lys Ala Val Val Ile Leu Val Thr Asp Val
1790                1795                1800

Ser Val Asp Ser Val Asp Ala Ala Asp Ala Ala Arg Ser Asn
1805                1810                1815

Arg Val Thr Val Phe Pro Ile Gly Ile Gly Asp Arg Tyr Asp Ala
1820                1825                1830

Ala Gln Leu Arg Ile Leu Ala Gly Pro Ala Gly Asp Ser Asn Val
1835                1840                1845

Val Lys Leu Gln Arg Ile Glu Asp Leu Pro Thr Met Val Thr Leu
1850                1855                1860

Gly Asn Ser Phe Leu His Lys Leu Cys Ser Gly Phe Val Arg Ile
1865                1870                1875

Cys Met Asp Glu Asp Gly Asn Glu Lys Arg Pro Gly Asp Val Trp
1880                1885                1890

Thr Leu Pro Asp Gln Cys His Thr Val Thr Cys Gln Pro Asp Gly
1895                1900                1905

Gln Thr Leu Leu Lys Ser His Arg Val Asn Cys Asp Arg Gly Leu
1910                1915                1920

Arg Pro Ser Cys Pro Asn Ser Gln Ser Pro Val Lys Val Glu Glu
1925                1930                1935

Thr Cys Gly Cys Arg Trp Thr Cys Pro Cys Val Cys Thr Gly Ser
1940                1945                1950

Ser Thr Arg His Ile Val Thr Phe Asp Gly Gln Asn Phe Lys Leu
1955                1960                1965

Thr Gly Ser Cys Ser Tyr Val Leu Phe Gln Asn Lys Glu Gln Asp
1970                1975                1980

Leu Glu Val Ile Leu His Asn Gly Ala Cys Ser Pro Gly Ala Arg
1985                1990                1995

Gln Gly Cys Met Lys Ser Ile Glu Val Lys His Ser Ala Leu Ser
2000                2005                2010

Val Glu Leu His Ser Asp Met Glu Val Thr Val Asn Gly Arg Leu
2015                2020                2025

Val Ser Val Pro Tyr Val Gly Gly Asn Met Glu Val Asn Val Tyr
2030                2035                2040

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100
```

```
Thr Thr Asp Trp Lys Thr Leu Val Gln Glu Trp Thr Val Gln Arg
    2105            2110                2115

Pro Gly Gln Thr Cys Gln Pro Ile Leu Glu Glu Gln Cys Leu Val
    2120            2125                2130

Pro Asp Ser Ser His Cys Gln Val Leu Leu Pro Leu Phe Ala
    2135            2140                2145

Glu Cys His Lys Val Leu Ala Pro Ala Thr Phe Tyr Ala Ile Cys
    2150            2155                2160

Gln Gln Asp Ser Cys His Gln Glu Gln Val Cys Glu Val Ile Ala
    2165            2170                2175

Ser Tyr Ala His Leu Cys Arg Thr Asn Gly Val Cys Val Asp Trp
    2180            2185                2190

Arg Thr Pro Asp Phe Cys Ala Met Ser Cys Pro Pro Ser Leu Val
    2195            2200                2205

Tyr Asn His Cys Glu His Gly Cys Pro Arg His Cys Asp Gly Asn
    2210            2215                2220

Val Ser Ser Cys Gly Asp His Pro Ser Glu Gly Cys Phe Cys Pro
    2225            2230                2235

Pro Asp Lys Val Met Leu Glu Gly Ser Cys Val Pro Glu Glu Ala
    2240            2245                2250

Cys Thr Gln Cys Ile Gly Glu Asp Gly Val Gln His Gln Phe Leu
    2255            2260                2265

Glu Ala Trp Val Pro Asp His Gln Pro Cys Gln Ile Cys Thr Cys
    2270            2275                2280

Leu Ser Gly Arg Lys Val Asn Cys Thr Thr Gln Pro Cys Pro Thr
    2285            2290                2295

Ala Lys Ala Pro Thr Cys Gly Leu Cys Glu Val Ala Arg Leu Arg
    2300            2305                2310

Gln Asn Ala Asp Gln Cys Cys Pro Glu Tyr Glu Cys Val Cys Asp
    2315            2320                2325

Pro Val Ser Cys Asp Leu Pro Pro Val Pro His Cys Glu Arg Gly
    2330            2335                2340

Leu Gln Pro Thr Leu Thr Asn Pro Gly Glu Cys Arg Pro Asn Phe
    2345            2350                2355

Thr Cys Ala Cys Arg Lys Glu Glu Cys Lys Arg Val Ser Pro Pro
    2360            2365                2370

Ser Cys Pro Pro His Arg Leu Pro Thr Leu Arg Lys Thr Gln Cys
    2375            2380                2385

Cys Asp Glu Tyr Glu Cys Ala Cys Asn Cys Val Asn Ser Thr Val
    2390            2395                2400

Ser Cys Pro Leu Gly Tyr Leu Ala Ser Thr Ala Thr Asn Asp Cys
    2405            2410                2415

Gly Cys Thr Thr Thr Thr Cys Leu Pro Asp Lys Val Cys Val His
    2420            2425                2430

Arg Ser Thr Ile Tyr Pro Val Gly Gln Phe Trp Glu Glu Gly Cys
    2435            2440                2445

Asp Val Cys Thr Cys Thr Asp Met Glu Asp Ala Val Met Gly Leu
    2450            2455                2460

Arg Val Ala Gln Cys Ser Gln Lys Pro Cys Glu Asp Ser Cys Arg
    2465            2470                2475

Ser Gly Phe Thr Tyr Val Leu His Glu Gly Glu Cys Cys Gly Arg
    2480            2485                2490

Cys Leu Pro Ser Ala Cys Glu Val Val Thr Gly Ser Pro Arg Gly
```

| | | | 2495 | | | | 2500 | | | | 2505 | | | |

Asp Ser Gln Ser Ser Trp Lys Ser Val Gly Ser Gln Trp Ala Ser
        2510                    2515                    2520

Pro Glu Asn Pro Cys Leu Ile Asn Glu Cys Val Arg Val Lys Glu
        2525                    2530                2535

Glu Val Phe Ile Gln Gln Arg Asn Val Ser Cys Pro Gln Leu Glu
        2540                    2545                2550

Val Pro Val Cys Pro Ser Gly Phe Gln Leu Ser Cys Lys Thr Ser
        2555                    2560                2565

Ala Cys Cys Pro Ser Cys Arg Cys Glu Arg Met Glu Ala Cys Met
        2570                    2575                2580

Leu Asn Gly Thr Val Ile Gly Pro Gly Lys Thr Val Met Ile Asp
        2585                    2590                2595

Val Cys Thr Thr Cys Arg Cys Met Val Gln Val Gly Val Ile Ser
        2600                    2605                2610

Gly Phe Lys Leu Glu Cys Arg Lys Thr Thr Cys Asn Pro Cys Pro
        2615                    2620                2625

Leu Gly Tyr Lys Glu Glu Asn Asn Thr Gly Glu Cys Cys Gly Arg
        2630                    2635                2640

Cys Leu Pro Thr Ala Cys Thr Ile Gln Leu Arg Gly Gly Gln Ile
        2645                    2650                2655

Met Thr Leu Lys Arg Asp Glu Thr Leu Gln Asp Gly Cys Asp Thr
        2660                    2665                2670

His Phe Cys Lys Val Asn Glu Arg Gly Glu Tyr Phe Trp Glu Lys
        2675                    2680                2685

Arg Val Thr Gly Cys Pro Pro Phe Asp Glu His Lys Cys Leu Ala
        2690                    2695                2700

Glu Gly Gly Lys Ile Met Lys Ile Pro Gly Thr Cys Cys Asp Thr
        2705                    2710                2715

Cys Glu Glu Pro Glu Cys Asn Asp Ile Thr Ala Arg Leu Gln Tyr
        2720                    2725                2730

Val Lys Val Gly Ser Cys Lys Ser Glu Val Glu Val Asp Ile His
        2735                    2740                2745

Tyr Cys Gln Gly Lys Cys Ala Ser Lys Ala Met Tyr Ser Ile Asp
        2750                    2755                2760

Ile Asn Asp Val Gln Asp Gln Cys Ser Cys Cys Ser Pro Thr Arg
        2765                    2770                2775

Thr Glu Pro Met Gln Val Ala Leu His Cys Thr Asn Gly Ser Val
        2780                    2785                2790

Val Tyr His Glu Val Leu Asn Ala Met Glu Cys Lys Cys Ser Pro
        2795                    2800                2805

Arg Lys Cys Ser Lys
        2810

<210> SEQ ID NO 3
<211> LENGTH: 2813
<212> TYPE: PRT
<213> ORGANISM: Homo sapiens
<220> FEATURE:
<221> NAME/KEY: PEPTIDE
<222> LOCATION: (1)..(2813)

<400> SEQUENCE: 3

Met Ile Pro Ala Arg Phe Ala Gly Val Leu Leu Ala Leu Ala Leu Ile
1               5                   10                  15

-continued

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu

-continued

```
            435                 440                 445
Pro Gly Leu His Asn Ser Leu Val Lys Leu Lys His Gly Ala Gly Val
450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                    485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
        530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
        610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
        770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
        850                 855                 860
```

```
Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260
```

-continued

Glu Pro Pro Leu His Asp Phe Tyr Cys Ser Arg Leu Leu Asp Leu
1265                1270                1275

Val Phe Leu Leu Asp Gly Ser Arg Leu Ser Glu Ala Glu Phe
1280                1285                1290

Glu Val Leu Lys Ala Phe Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Thr Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg

```
                1655                1660                1665

Cys Cys Ser Gly Glu Gly Leu Gln Ile Pro Thr Leu Ser Pro Ala
            1670                1675                1680

Pro Asp Cys Ser Gln Pro Leu Asp Val Ile Leu Leu Leu Asp Gly
            1685                1690                1695

Ser Ser Ser Phe Pro Ala Ser Tyr Phe Asp Glu Met Lys Ser Phe
            1700                1705                1710

Ala Lys Ala Phe Ile Ser Lys Ala Asn Ile Gly Pro Arg Leu Thr
            1715                1720                1725

Gln Val Ser Val Leu Gln Tyr Gly Ser Ile Thr Thr Ile Asp Val
            1730                1735                1740

Pro Trp Asn Val Val Pro Glu Lys Ala His Leu Leu Ser Leu Val
            1745                1750                1755

Asp Val Met Gln Arg Glu Gly Gly Pro Ser Gln Ile Gly Asp Ala
            1760                1765                1770

Leu Gly Phe Ala Val Arg Tyr Leu Thr Ser Glu Met His Gly Ala
            1775                1780                1785

Arg Pro Gly Ala Ser Lys Ala Val Val Ile Leu Val Thr Asp Val
            1790                1795                1800

Ser Val Asp Ser Val Asp Ala Ala Ala Asp Ala Ala Arg Ser Asn
            1805                1810                1815

Arg Val Thr Val Phe Pro Ile Gly Ile Gly Asp Arg Tyr Asp Ala
            1820                1825                1830

Ala Gln Leu Arg Ile Leu Ala Gly Pro Ala Gly Asp Ser Asn Val
            1835                1840                1845

Val Lys Leu Gln Arg Ile Glu Asp Leu Pro Thr Met Val Thr Leu
            1850                1855                1860

Gly Asn Ser Phe Leu His Lys Leu Cys Ser Gly Phe Val Arg Ile
            1865                1870                1875

Cys Met Asp Glu Asp Gly Asn Glu Lys Arg Pro Gly Asp Val Trp
            1880                1885                1890

Thr Leu Pro Asp Gln Cys His Thr Val Thr Cys Gln Pro Asp Gly
            1895                1900                1905

Gln Thr Leu Leu Lys Ser His Arg Val Asn Cys Asp Arg Gly Leu
            1910                1915                1920

Arg Pro Ser Cys Pro Asn Ser Gln Ser Pro Val Lys Val Glu Glu
            1925                1930                1935

Thr Cys Gly Cys Arg Trp Thr Cys Pro Cys Val Cys Thr Gly Ser
            1940                1945                1950

Ser Thr Arg His Ile Val Thr Phe Asp Gly Gln Asn Phe Lys Leu
            1955                1960                1965

Thr Gly Ser Cys Ser Tyr Val Leu Phe Gln Asn Lys Glu Gln Asp
            1970                1975                1980

Leu Glu Val Ile Leu His Asn Gly Ala Cys Ser Pro Gly Ala Arg
            1985                1990                1995

Gln Gly Cys Met Lys Ser Ile Glu Val Lys His Ser Ala Leu Ser
            2000                2005                2010

Val Glu Leu His Ser Asp Met Glu Val Thr Val Asn Gly Arg Leu
            2015                2020                2025

Val Ser Val Pro Tyr Val Gly Gly Asn Met Glu Val Asn Val Tyr
            2030                2035                2040

Gly Ala Ile Met His Glu Val Arg Phe Asn His Leu Gly His Ile
            2045                2050                2055
```

-continued

Phe Thr Phe Thr Pro Gln Asn Asn Glu Phe Gln Leu Gln Leu Ser
    2060            2065            2070

Pro Lys Thr Phe Ala Ser Lys Thr Tyr Gly Leu Cys Gly Ile Cys
    2075            2080            2085

Asp Glu Asn Gly Ala Asn Asp Phe Met Leu Arg Asp Gly Thr Val
    2090            2095            2100

Thr Thr Asp Trp Lys Thr Leu Val Gln Glu Trp Thr Val Gln Arg
    2105            2110            2115

Pro Gly Gln Thr Cys Gln Pro Ile Leu Glu Glu Gln Cys Leu Val
    2120            2125            2130

Pro Asp Ser Ser His Cys Gln Val Leu Leu Leu Pro Leu Phe Ala
    2135            2140            2145

Glu Cys His Lys Val Leu Ala Pro Ala Thr Phe Tyr Ala Ile Cys
    2150            2155            2160

Gln Gln Asp Ser Cys His Gln Glu Gln Val Cys Glu Val Ile Ala
    2165            2170            2175

Ser Tyr Ala His Leu Cys Arg Thr Asn Gly Val Cys Val Asp Trp
    2180            2185            2190

Arg Thr Pro Asp Phe Cys Ala Met Ser Cys Pro Pro Ser Leu Val
    2195            2200            2205

Tyr Asn His Cys Glu His Gly Cys Pro Arg His Cys Asp Gly Asn
    2210            2215            2220

Val Ser Ser Cys Gly Asp His Pro Ser Glu Gly Cys Phe Cys Pro
    2225            2230            2235

Pro Asp Lys Val Met Leu Glu Gly Ser Cys Val Pro Glu Glu Ala
    2240            2245            2250

Cys Thr Gln Cys Ile Gly Glu Asp Gly Val Gln His Gln Phe Leu
    2255            2260            2265

Glu Ala Trp Val Pro Asp His Gln Pro Cys Gln Ile Cys Thr Cys
    2270            2275            2280

Leu Ser Gly Arg Lys Val Asn Cys Thr Thr Gln Pro Cys Pro Thr
    2285            2290            2295

Ala Lys Ala Pro Thr Cys Gly Leu Cys Glu Val Ala Arg Leu Arg
    2300            2305            2310

Gln Asn Ala Asp Gln Cys Cys Pro Glu Tyr Glu Cys Val Cys Asp
    2315            2320            2325

Pro Val Ser Cys Asp Leu Pro Pro Val Pro His Cys Glu Arg Gly
    2330            2335            2340

Leu Gln Pro Thr Leu Thr Asn Pro Gly Glu Cys Arg Pro Asn Phe
    2345            2350            2355

Thr Cys Ala Cys Arg Lys Glu Glu Cys Lys Arg Val Ser Pro Pro
    2360            2365            2370

Ser Cys Pro Pro His Arg Leu Pro Thr Leu Arg Lys Thr Gln Cys
    2375            2380            2385

Cys Asp Glu Tyr Glu Cys Ala Cys Asn Cys Val Asn Ser Thr Val
    2390            2395            2400

Ser Cys Pro Leu Gly Tyr Leu Ala Ser Thr Ala Thr Asn Asp Cys
    2405            2410            2415

Gly Cys Thr Thr Thr Thr Cys Leu Pro Asp Lys Val Cys Val His
    2420            2425            2430

Arg Ser Thr Ile Tyr Pro Val Gly Gln Phe Trp Glu Glu Gly Cys
    2435            2440            2445

-continued

```
Asp Val Cys Thr Cys Thr Asp Met Glu Asp Ala Val Met Gly Leu
    2450                2455                2460
Arg Val Ala Gln Cys Ser Gln Lys Pro Cys Glu Asp Ser Cys Arg
2465                2470                2475
Ser Gly Phe Thr Tyr Val Leu His Glu Gly Glu Cys Cys Gly Arg
    2480                2485                2490
Cys Leu Pro Ser Ala Cys Glu Val Val Thr Gly Ser Pro Arg Gly
2495                2500                2505
Asp Ser Gln Ser Ser Trp Lys Ser Val Gly Ser Gln Trp Ala Ser
    2510                2515                2520
Pro Glu Asn Pro Cys Leu Ile Asn Glu Cys Val Arg Val Lys Glu
2525                2530                2535
Glu Val Phe Ile Gln Gln Arg Asn Val Ser Cys Pro Gln Leu Glu
    2540                2545                2550
Val Pro Val Cys Pro Ser Gly Phe Gln Leu Ser Cys Lys Thr Ser
2555                2560                2565
Ala Cys Cys Pro Ser Cys Arg Cys Glu Arg Met Glu Ala Cys Met
    2570                2575                2580
Leu Asn Gly Thr Val Ile Gly Pro Gly Lys Thr Val Met Ile Asp
2585                2590                2595
Val Cys Thr Thr Cys Arg Cys Met Val Gln Val Gly Val Ile Ser
    2600                2605                2610
Gly Phe Lys Leu Glu Cys Arg Lys Thr Thr Cys Asn Pro Cys Pro
2615                2620                2625
Leu Gly Tyr Lys Glu Glu Asn Asn Thr Gly Glu Cys Cys Gly Arg
    2630                2635                2640
Cys Leu Pro Thr Ala Cys Thr Ile Gln Leu Arg Gly Gly Gln Ile
2645                2650                2655
Met Thr Leu Lys Arg Asp Glu Thr Leu Gln Asp Gly Cys Asp Thr
    2660                2665                2670
His Phe Cys Lys Val Asn Glu Arg Gly Glu Tyr Phe Trp Glu Lys
2675                2680                2685
Arg Val Thr Gly Cys Pro Pro Phe Asp Glu His Lys Cys Leu Ala
    2690                2695                2700
Glu Gly Gly Lys Ile Met Lys Ile Pro Gly Thr Cys Cys Asp Thr
2705                2710                2715
Cys Glu Glu Pro Glu Cys Asn Asp Ile Thr Ala Arg Leu Gln Tyr
    2720                2725                2730
Val Lys Val Gly Ser Cys Lys Ser Glu Val Glu Val Asp Ile His
2735                2740                2745
Tyr Cys Gln Gly Lys Cys Ala Ser Lys Ala Met Tyr Ser Ile Asp
    2750                2755                2760
Ile Asn Asp Val Gln Asp Gln Cys Ser Cys Cys Ser Pro Thr Arg
2765                2770                2775
Thr Glu Pro Met Gln Val Ala Leu His Cys Thr Asn Gly Ser Val
    2780                2785                2790
Val Tyr His Glu Val Leu Asn Ala Met Glu Cys Lys Cys Ser Pro
2795                2800                2805
Arg Lys Cys Ser Lys
2810
```

PRODUCTION OF RECOMBINANT VON WILLEBRAND FACTOR IN A BIOREACTOR

RELATED APPLICATION DATA

This application is the United States national stage entry under 35 U.S.C. § 371 of International Application No. PCT/AU2015/050170, filed on Apr. 14, 2015 and published as WO 2015/188224 A9, which claims priority to European Patent Application No. 14172338.7, filed on Jun. 13, 2014. The contents of these applications are each incorporated herein by reference in their entirety.

SEQUENCE LISTING

The present application is filed with a Sequence Listing in electronic form. The entire contents of the Sequence Listing are hereby incorporated by reference.

FIELD OF INVENTION

The present invention relates to improved methods for the recombinant production of von Willebrand factor (vWF) in a bioreactor by separating different species of vWF multimers during fermentation.

BACKGROUND

Biotechnology offers the promise of producing low cost biopharmaceutical products, including recombinant proteins. Many therapeutic proteins, such as coagulation factors, have therapeutic potential if they can be produced recombinantly in a way that retains their biological activity, and produces sufficient yields to be commercially viable. For instance, recombinantly produced coagulation factors such as von Willebrand Factor (vWF) have the potential to treat a wide variety of bleeding disorders. However, this potential has not been adequately met partly because of the inherent complexity of naturally-occurring biological molecules and the variety of limitations associated with the synthesis of their recombinant protein counterparts in genetically engineered cells. Therefore, a strong need exists in the art for improved methods of producing recombinant, highly biologically active therapeutic proteins such as vWF.

Recombinant therapeutic proteins are usually expressed in eukaryotic cells which are cultivated in bioreactors of varying size. Several modes of operating such bioreactors are known in the field like fed-batch processes and perfusion processes. In such fermentation processes it is desirable to maintain high cell viability and cell density in order to obtain the desired recombinant protein in a concentrated form which facilitates subsequent purification.

WO 2008/006494 discloses a perfusion process in which the accumulation of the desired therapeutic protein in the cell culture supernatant is achieved to high concentrations by feeding culture media components to the cell culture in a bioreactor and wherein the cell culture comprising the cells, the therapeutic protein and the cell culture medium is circulated over a separation system wherein the separation system separates the therapeutic protein from substances of lower molecular weight than the therapeutic protein like from metabolites. The molecular weight cut-off (MWCO) of the substances to be separated from the therapeutic protein of interest in WO 2008/006494 is between 5,000 Da to 500,000 Da preferably at most 100,000 Da.

EP2171034 discloses a method of producing a biopolymer in a continuous fermentation process wherein an impurity filter is used which allows impurities with a molecular weight below the molecular weight of the biopolymer of interest to be removed from the biopolymer of interest in the bioreactor. This patent also discloses a continuous fermentation process in which a combination of a filter unit equipped with an impurity filter is combined with a filter unit equipped with a product filter which will let the biopolymer of interest pass in order to harvest the biopolypeptide of interest. Impurity filter pore sizes of up to 80,000 Da are described whereby the preferred range is 2,000 Da to 15,000 Da. As biopolymers of interest only polypeptides with a given molecular weight are described. The largest biopolymer of interest disclosed is Factor VIII having a molecular weight of about 280,000 Da.

BRIEF SUMMARY OF THE INVENTION

Figure 1:
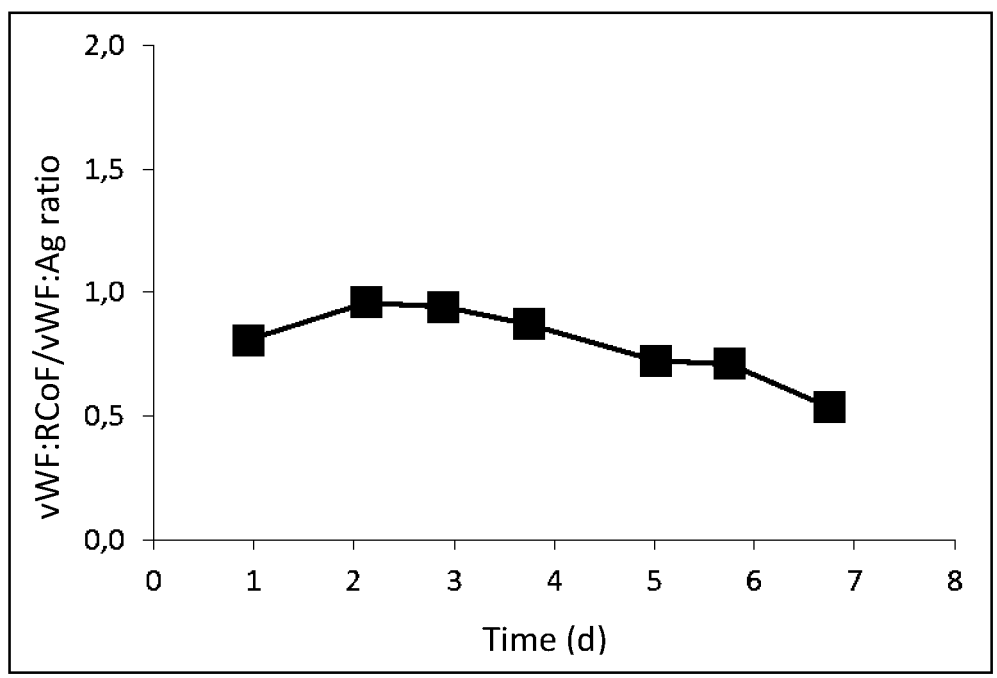
FIG. 1 shows the ratio of vWF Ristocetin Cofactor activity over vWF antigen (vWF:RCoF/vWF:Ag) in the bioreactor during the batch process.

The present invention relates to the surprising discovery that a separation system can be used in a bioreactor during a fermentation process to separate certain multimeric forms of vWF from other multimeric forms of vWF. Such different multimeric forms of vWF with different molecular weight do have different properties and/or different biological activities. Such separation already taking place during the up-stream fermentation step of manufacturing greatly reduces the purification effort in downstream processing.

Embodiments of the present invention therefore include methods for producing a recombinant von Willebrand factor (vWF).

One embodiment of the present invention is a process for manufacturing a recombinant von Willebrand factor (vWF) by culturing host cells in a bioreactor in a cell culture medium, wherein the host cells produce recombinant vWF which is secreted into the cell culture medium and wherein the vWF in the cell culture medium comprises vWF multimers of different size,
wherein at least one cell culture medium component is fed to the cell culture medium and wherein the cell culture comprising the cells, the recombinant vWF and the cell culture medium is pumped over a separation system and wherein the separation system separates the vWF multimers into at least
a permeate fraction which is enriched in low molecular weight (LMW) multimers of vWF and reduced in high molecular weight (HMW) multimers of vWF as compared to the vWF multimers in the cell culture supernatant before separation and
a retentate fraction which is reduced in low molecular weight (LMW) multimers of vWF and enriched in high molecular weight (HMW) multimers of vWF as compared to the vWF multimers in the cell culture supernatant before separation In one embodiment of the invention the two fractions of the vWF do have different biological activities.

In another embodiment of the invention the desired fraction of the recombinant vWF intended to be purified further is the permeate.

In another embodiment the recombinant VWF in the permeate is enriched in low molecular weight (LMW) vWF multimers and reduced in high molecular weight (HMW) vWF multimers, wherein the LMW vWF multimers correspond to bands 1 to 5 and the HMW vWF multimers correspond to bands 11 and higher in a densitometric vWF analysis according to Ott et al. (Am J Clin Pathol 2010; 133:322-330).

In another embodiment of the invention the LMW vWF Multimer Ratio in the permeate is equal to or below 0.9, or in other words the ratio of the "accumulated pixel intensities related to standard human plasma" of vWF multimer bands 1 to 5 in the retentate divided by the "accumulated pixel intensities related to standard human plasma" of vWF multimer bands 1 to 5 in the permeate is below 0.9, wherein the "accumulated pixel intensities related to standard human plasma" of vWF multimer bands 1 to 5 HMW refers to the numerical value which is obtained when the amount of bands 1 to 5 as determined in a densitometric vWF analysis according to Ott et al. (Am J Clin Pathol 2010; 133:322-330) is divided by the amount of bands 1 to 5 of a standard human plasma as determined in a densitometric vWF analysis according to Ott et al. (Am J Clin Pathol 2010; 133:322-330). Preferentially standard human plasma (SHP) (Siemens, Standard Human Plasma, ORKL17) is used.

In another embodiment of the invention the desired fraction of the recombinant vWF intended to be purified further is the retentate.

In another embodiment of the invention the HMW vWF Multimer Ratio in the retentate is equal to or above 1.1, or in other words the ratio of the "accumulated pixel intensities related to standard human plasma" of vWF multimer bands 11 and higher in the retentate divided by the "accumulated pixel intensities related to standard human plasma" of vWF multimer bands 11 and higher in the permeate is above 1.2, wherein the "accumulated pixel intensities related to standard human plasma" of vWF multimer bands 11 and higher refers to the numerical value which is obtained when the amount of bands 11 and higher as determined in a densitometric vWF analysis according to Ott et al. (Am J Clin Pathol 2010; 133:322-330) is divided by the amount of bands 11 and higher of a standard human plasma as determined in a densitometric vWF analysis according to Ott et al. (Am J Clin Pathol 2010; 133:322-330). Preferentially standard human plasma (SHP) (Siemens, Standard Human Plasma, ORKL17) is used.

In certain embodiments the molecular weight cut off size of the separation system is about 0.05 µm to 1 µm.

In other embodiments of the invention the molecular weight cut off size of the separation system is about 550,000 to 1,000,000 Da.

In another embodiment of the invention the molecular weight cut off size of the separation system is about 750,000 Da.

In another embodiment of the invention a second separation takes place wherein the retentate as obtained in any of the processes described above is subjected to a second separation wherein ultra-large vWF multimers are enriched in said retentate, providing a second permeate in which the proportion of ultra-large vWF multimers in the total vWF multimer amount is reduced as compared to the proportion of ultra-large vWF multimers in the total vWF multimer amount in the retentate before said second separation.

In one embodiment the second separation is done in parallel with the first separation and in another embodiment the second separation is done after the first separation.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight, length, or other unit described herein.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

By "biological activity" is meant a measurable function of vWF which vWF performs also in vivo when administered to a human being. As used herein, the terms "function" and "functional" and the like refer to a biological, enzymatic, or therapeutic function of vWF. The biological activity of vWF can for example be determined by the artisan using methods to determine the ristocetin co-factor activity (vWF:RCoF) (Federici A B et al. 2004. Haematologica 89:77-85), the binding of vWF to GP Ib of the platelet glycoprotein complex Ib-V-IX (Sucker et al. 2006. Clin Appl Thromb Hemost. 12:305-310), a collagen binding assay (Kallas & Talpsep. 2001. Annals of Hematology 80:466-471) or a FVIII binding assay. FVIII binding may be determined for example by Biacore analysis.

By "bioreactor" is meant any manufactured or engineered device or system that provides and supports a biologically active environment for cell culture which allows the cells to grow and produce the product of interest. Bioreactors in general measure and regulate the physical and chemical parameters which are needed to generate this biological active environment. Bioreactors can be operated in different modes as batch, fed-batch or continuous. Bioreactors which are operated in continuous mode are additionally equipped with a media inlet and a device for separating the cells from the supernatant. Commonly bioreactors are cylindrical or cubic, ranging in size from milliliters to cubic meters, and are often made of stainless steel or plastic.

The term "host cell" includes an individual cell or cell culture that can be or has been a recipient of an introduced, recombinant vector, isolated polynucleotide, or polypeptide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide. A host cell which comprises a recombinant vector is a recombinant host cell. Specific host cells are defined below.

A "separation system" according to the invention means a device which can be used to retain host cells within a bioreactor during a fermentation process wherein at least part of the cell culture supernatant is separated from the host cells by means of a separation system comprising a filter which has a certain molecular weight cut off. Host cells and vWF multimers above a certain molecular weight are retained by said filter with a certain molecular weight cut off. Small molecules, nutrients and metabolites as well as vWF multimers below a certain molecular weight cut off can pass said filter with a certain molecular weight cut off. Cell retention within the culture vessel may be achieved using a number of cell retention devices. Different separation principles may be used for this process. The methods could be based on gravity settling, acoustic settling, centrifugal settling or filtration. The following sets of apparatus may all be used for this process: internal or external filters like internal or external spin filters (e.g. Spinfilter P from Sartorius), external cross flow filters, external or internal hollow fiber cartridge filters (e.g. alternating tangential flow (ATF) from Refine). The pore size of the filter with a certain molecular weight cut off (MWCO) is preferably between 0.05 μm and 1.0 μm. The MWCO is preferably equal or above 500,000 Da, or equal or above 550,000 Da, or equal or above 600,000 Da, or equal or above 650,000 Da, or equal or above 700,000 Da, or about 750,000 Da, or equal or below 1,000,000 Da, or equal or below 950,000 Da or equal or below 900,000 Da, or equal or below 850,000 Da, or equal or below 800,000 Da. It is to be understood that the above lower molecular weight cut off values can be combined with the above mentioned upper molecular weight cut offs to define ranges for the preferred parts with a certain molecular weight cut off like for example a range between equal or above 500,000 Da up to 1,000,000 Da or between 550,000 Da up to 1,000,000 Da etc.

The part of the cell culture that has passed the separation device is called the "permeate" whereas the part of the cell culture which is retained by the separation device is called the "retentate".

A MWCO of 500,000 used in a separation system means that proteins below 500,000 Da pass the separation and are enriched in the permeate, whereas proteins above 500,000 Da are retained by the filter and are therefore enriched in the retentate.

This separation can be used to enrich for certain fractions of vWF multimers with different molecular size which do have different biological activities.

"Substantially" or "essentially" means nearly totally or completely, for instance, 95%, 96%, 97%, 98%, 99% or greater of some given quantity.

The term "von Willebrand Factor" or "vWF", as used herein, refers to any polypeptide having the biological activity of wild type vWF or at least a partial biological activity of vWF. The gene encoding wild type vWF is transcribed into a 9 kb mRNA which is translated into a pre-propolypeptide of 2813 amino acids with an estimated molecular weight of 310,000 Da. The pre-propolypeptide consists of 2813 amino acids and contains a 22 amino acids signal peptide, a 741 amino acid pro-polypeptide and the mature subunit. Cleavage of the 741 amino acids pro-polypeptide from the N-terminus results in mature vWF consisting of 2050 amino acids. The cDNA sequence of wild type pre-pro-vWF is shown in SEQ ID NO: 1. The amino acid sequence of wild type pre-pro-vWF is shown in SEQ ID NO:2. The term "vWF" as used herein refers to the mature form of vWF unless indicated otherwise.

The pro-polypeptide of wild type vWF comprises multiple domains which are arranged in the following order: D1-D2-D' D3-A1-A2-A3-D4-B1-B2-B3-C1-C2-CK The D1 and D2 domain represent the pro-peptide which is cleaved off to yield the mature vWF. The carboxy-terminal 90 residues comprise the "CK" domain that is homologous to the "cystine knot" superfamily of protein. These family members have a tendency to dimerise through disulfide bonds.

Preferably, wild type vWF comprises the amino acid sequence of wild type vWF as shown in SEQ ID NO:2. Also encompassed are additions, insertions, N-terminal, C-terminal or internal deletions of vWF as long as at least a partial biological activity of vWF is retained. The biological activity of wild-type vWF can be determined by the artisan using methods for ristocetin co-factor activity (Federici A B et al. 2004. Haematologica 89:77-85), binding of vWF to GP Ibα of the platelet glycoprotein complex Ib-V-IX (Sucker et al. 2006. Clin Appl Thromb Hemost. 12:305-310), a collagen binding assay (Kallas & Talpsep. 2001. Annals of Hematology 80:466-471) or a FVIII binding assay Certain embodiments may include the recombinant production of wild-type vWF as for example described in WO 2010/048275, or variants thereof, for example, in which one or more amino acid deletions, additions, and/or substitutions have been introduced to increase or decrease at least one biological activity of the protein.

Accordingly, certain embodiments may employ any one or more of these vWF related sequences, including combinations and variants thereof. Also included are vWF-related sequences from other organisms, such as other mammals described herein and known in the art.

In certain embodiments the term "vWF" includes "fusion proteins" of vWF, preferably "fusion proteins" of a vWF protein and a "heterologous" fusion partner. Also included are fusion proteins or modified proteins that comprise a heterologous fusion partner or heterologous sequence and at least one minimal fragment or portion of a vWF protein.

As used herein, a "fusion protein" includes a vWF protein or fragment thereof linked to either another (e.g., different) vWF protein (e.g., to create multiple fragments), to a vWF protein, or to both. A "non-vWF protein" refers to a "heterologous polypeptide" having an amino acid sequence corresponding to a protein which is different from a vWF protein, and which can be derived from the same or a different organism. The vWF protein of the fusion protein can correspond to all or a portion of a biologically active vWF protein amino acid sequence. In certain embodiments, a vWF fusion protein includes at least one (or two, three, etc.) biologically active portion(s) of a vWF protein.

More generally, fusion to heterologous sequences, such as albumin or immunoglobulins or fragments derived from immunoglobulins without an antigen binding domain, such as the Fc fragment, may be utilized to remove unwanted characteristics or to improve the desired characteristics (e.g., pharmacokinetic properties) of a vWF. For example, fusion to a heterologous sequence may increase chemical stability, decrease immunogenicity, improve in vivo targeting, and/or increase half-life in circulation of a vWF protein.

"Albumin", as used herein, includes polypeptides of the albumin family of proteins such as human serum albumin and bovine serum albumin, including variants and derivatives thereof, such as genetically engineered or chemically modified albumin variants and fragments of albumin proteins. The albumin portion of a fusion protein may be derived from any vertebrate, especially any mammal, for example human, cow, sheep, or pig. Non-mammalian albumins include, but are not limited to, hen and salmon. The albumin portion of the albumin-linked polypeptide may be from a different animal than the vWF protein portion of the fusion protein.

The albumin family of proteins, included within the term "albumin" used herein, comprise evolutionarily related serum transport proteins, for example, albumin, alpha-fetoprotein (AFP; Beattie & Dugaiczyk, Gene. 20:415-422, 1982), afamin (AFM; Lichenstein et al., J. Biol. Chem. 269:18149-18154, 1994), and vitamin D binding protein (DBP; Cooke & David, J. Clin. Invest. 76:2420-2424, 1985). Alpha-fetoprotein has been claimed to enhance the half-life of an attached therapeutic polypeptide (see WO 2005/024044). Their genes represent a multigene cluster with structural and functional similarities mapping to the same chromosomal region in humans, mice and rat. Some embodiments of the invention, therefore, may use such albumin family members, or fragments and variants thereof as defined herein, as part of a fusion protein. Albumin family members of the therapeutic fusion proteins of the invention may also include naturally-occurring polymorphic variants of AFP, AFM and DBP.

VWF protein, or a fragment or variant thereof, may be fused to a human serum albumin polypeptide, or a fragment or variant thereof (see, e.g. WO 2009/156137). Human serum albumin (HSA, or HA), is a protein of 585 amino acids in its mature form, and is responsible for a significant proportion of the osmotic pressure of serum and also functions as a carrier of endogenous and exogenous ligands. Among other benefits, fusion to HSA or a fragment or variant thereof can increase the shelf-life, serum half-life, and/or therapeutic activity of the vWF proteins described herein.

Preferably a fusion protein comprises albumin as the C-terminal portion, and a vWF protein as the N-terminal portion. In other embodiments, the fusion protein has vWF proteins fused to both the N-terminus and the C-terminus of albumin.

A peptide linker sequence may be employed to separate the components of a fusion protein. For instance, peptide linkers can separate the components by a distance sufficient to ensure that each polypeptide folds into its secondary and tertiary structures. Such a peptide linker sequence may be incorporated into the fusion protein using standard techniques described herein and well-known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. Nos. 4,935,233 and 4,751,180.

One or more of the non-peptide or peptide linkers are optional. For instance, linker sequences may not be required in a fusion protein where the first and second polypeptides have non-essential N-terminal and/or C-terminal amino acid regions that can be used to separate the functional domains and prevent steric interference.

Certain embodiments of the present invention also contemplate the use of modified vWF proteins, including modifications that improved the desired characteristics of the protein, as described herein. Modifications of vWF proteins include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include PEGylation of a vWF protein (see, e.g., Veronese and Harris, Advanced Drug Delivery Reviews 54: 453-456, 2002, herein incorporated by reference). VWF variants which are chemically conjugated to biologically acceptable polymers are described for example in WO 2006/071801.

The invention may also be used with "variants" of vWF proteins. The term protein "variant" includes proteins that are distinguished from SEQ ID NO:2 by the addition, deletion, and/or substitution of at least one amino acid residue, and which typically retain one or more activities of the reference protein. It is within the skill of those in the art to identify amino acids suitable for substitution and to design variants with substantially unaltered, improved, or decreased activity, relative to a reference sequence.

A protein variant may be distinguished from a reference sequence by one or more substitutions, which may be conservative or non-conservative, as described herein and known in the art. In certain embodiments, the protein variant comprises conservative substitutions and, in this regard, it is well understood in the art that some amino acids may be changed to others with broadly similar properties without changing the nature of the activity of the protein.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected.

As noted above, biologically active variant proteins may contain conservative amino acid substitutions at various locations along their sequence, as compared to a reference residue. A "conservative amino acid substitution" includes one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. For the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 1 below.

TABLE 1

Amino acid sub-classification

| Sub-classes | Amino acids |
| --- | --- |
| Acidic | Aspartic acid, Glutamic acid |
| Basic Charged | Noncyclic: Arginine, |
| Small | Lysine; Cyclic: Histidine |
| Polar/neutral | Aspartic acid, Glutamic acid, Arginine, Lysine, Histidine |
| Polar/large | Glycine, Serine, Alanine, Threonine, Proline |
| Hydrophobic | Asparagine, Histidine, Glutamine, Cysteine, Serine, Threonine Asparagine, Glutamine |
| Aromatic | Tyrosine, Valine, |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a biologically active protein can readily be determined by assaying its chromogenic and/or coagulation activity, as described herein.

The terms "Low molecular weight vWF multimers" or "LMW vWF multimers" or "LMW vWF" are used synonymously and are meant to correspond to bands 1 to 5 in a densitometric vWF analysis according to Ott et al. (Am J Clin Pathol 2010; 133:322-330).

The terms "High molecular weight vWF multimers" or "HMW vWF multimers" or "HMW vWF" are used synonymously and are meant to correspond to bands 11 and higher in a densitometric vWF analysis according to Ott et al. (Am J Clin Pathol 2010; 133:322-330), wherein "higher" means band 11 and all larger vWF multimers.

"Ultra-large molecular weight vWF multimers" or "ULMW vWF multimers" are used synonymously and are meant to correspond to bands 20 and higher in a densitometric vWF analysis according to Ott et al. (Am J Clin Pathol 2010; 133:322-330), wherein "higher" means band 20 and all larger vWF multimers.

The term "HMW Multimer Ratio" refers to the ratio of the "accumulated pixel intensities related to standard human plasma" of vWF multimer bands 11 and higher in the retentate divided by the "accumulated pixel intensities related to standard human plasma" of vWF multimer bands 11 and higher in the permeate.

The term "accumulated pixel intensities related to standard human plasma" of vWF multimer bands 11 and higher refers to the numerical value which is obtained when the amount of bands 11 and higher as determined in a densitometric vWF analysis according to Ott et al. (Am J Clin Pathol 2010; 133:322-330) is divided by the amount of bands 11 and higher of a standard human plasma as determined in a densitometric vWF analysis according to Ott et al. (Am J Clin Pathol 2010; 133:322-330). Preferentially standard human plasma (SHP) (Siemens, Standard Human Plasma, ORKL17) is used.

The term "LMW Multimer Ratio" refers to the ratio of the "accumulated pixel intensities related to standard human plasma" of vWF multimer bands 1 to 5 in the retentate divided by the "accumulated pixel intensities related to standard human plasma" of vWF multimer bands 1 to 5 in the permeate.

The term "accumulated pixel intensities related to standard human plasma" of vWF multimer bands 1 to 5 HMW refers to the numerical value which is obtained when the amount of bands 1 to 5 as determined in a densitometric vWF analysis according to Ott et al. (Am J Clin Pathol 2010; 133:322-330) is divided by the amount of bands 1 to 5 of a standard human plasma as determined in a densitometric vWF analysis according to Ott et al. (Am J Clin Pathol 2010; 133:322-330). Preferentially standard human plasma (SHP) (Siemens, Standard Human Plasma, ORKL17) is used.

An LMW vWF Multimer Ratio in the permeate "below" the LMW vWF Multimer Ratio of the cell culture medium before separation is typically a "statistically significant" decreased ratio, and may include a decrease that is 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10 or more times (including all integers and decimal points and ranges in between and above 1, e.g., 5.5, 5.6, 5.7, 5.8, etc.) below the LMW vWF Multimer Ratio of the cell culture medium before separation.

An HMW vWF Multimer Ratio in the permeate "above" the HMW vWF Multimer Ratio of the cell culture medium before separation is typically a "statistically significant" increased ratio, and may include an increase that is 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10 or more times (including all integers and decimal points and ranges in between and above 1, e.g., 5.5, 5.6, 5.7, 5.8, etc.) above the HMW vWF Multimer Ratio of the cell culture medium before separation.

Expression and Purification of Proteins of the Invention

Embodiments of the present invention include methods and related compositions for expressing, collecting, and optionally purifying the vWF fractions described herein.

For instance, certain embodiments include methods for producing a vWF or variant thereof, comprising culturing a cell in a cell culture medium, optionally a mammalian cell, where the cell comprises at least one introduced polynucleotide that encodes the vWF, where said polynucleotide is operably linked to at least one regulatory element and expresses the protein and collecting the protein from the cell or cell culture medium.

Recombinant vWF or variants thereof can be conveniently prepared using standard protocols. As one general example, recombinant vWF may be prepared by a procedure including one or more of the steps of: (a) preparing a construct comprising a polynucleotide sequence that encodes a protein and that is operably linked to at least one regulatory element; (b) introducing the construct into a host cell; (c) culturing the host cell to express the polypeptide and (d) collecting or isolating the polypeptide from the host cell.

To express a vWF, a nucleotide sequence encoding the polypeptide, or a functional equivalent, may be inserted into an appropriate expression vector, i.e., a vector which contains the necessary elements for the transcription and translation of the inserted coding sequence. Methods which are well known to those skilled in the art may be used to construct expression vectors containing sequences encoding vWF and appropriate transcriptional and translational control elements. These methods include in vitro recombinant DNA techniques, synthetic techniques, and in vivo genetic recombination and are known in the art.

The "regulatory elements" or "regulatory sequences" present in an expression vector include those non-translated regions of the vector, e.g., enhancers, promoters, 5' and 3' un-translated regions, ribosome binding site(s), RNA splice sites (if intron-containing genomic DNA is present), polyadenylation site(s), transcriptional termination sequence(s), which interact with host cellular proteins to carry out transcription and translation. Such elements may vary in their strength and specificity.

Depending on the vector system and host utilized, any number of suitable transcription and translation elements, including constitutive and inducible promoters, may be used. For example, in mammalian cell systems, promoters from mammalian genes or from mammalian viruses are generally preferred.

Specific initiation signals may also be used to achieve more efficient translation of sequences encoding a polypeptide of interest. Such signals include the ATG initiation codon and adjacent sequences.

In cases where sequences encoding the vWF, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells. In addition, transcription enhancers, such as the Rous sarcoma virus (RSV) enhancer or the CMV promoter/enhancer, may be used to increase expression in mammalian host cells.

Suitable host cells are higher eukaryotic cells such as mammalian cells. Examples of useful mammalian host cell lines include monkey kidney CV1 line transformed by SV40 (COS-7, ATCC CRL 1651); human embryonic kidney line (e.g., HEK293 cells, 293 cells sub-cloned for growth in suspension culture; baby hamster kidney cells (BHK, ATCC CCL 10)); mouse sertoli cells; monkey kidney cells (CV1 ATCC CCL 70); African green monkey kidney cells (VERO cells, VERO-76, ATCC CRL-1587); COS cells, human cervical carcinoma cells (Hela cells, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB8065); mouse mammary tumor (MMT 060562, ATCC CCL51); TR1 cells; MRC 5 cells; FS4 cells; and a human hepatoma line (Hep G2). Other useful mammalian host cell lines include Chinese hamster ovary (CHO cells, including DHFR-CHO cells); and myeloma cell lines such as NS0 and Sp2/0.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) and DG44 (CHO cell line). Also useful are 3T3 cells, Namalwa cells, myelomas and fusions of myelomas with other cells.

Certain preferred mammalian cell expression systems include CHO and HEK293-cell based expression systems. Particular examples of CHO cells include CHO-K1 and CHO-S cells. Also included are host cells that can be grown on serum free medium, such as certain HEK293 cells and CHO cells.

In some embodiments, the host cells are capable of growing in suspension cultures. As used herein, suspension-competent cells are those that can grow in suspension without making large, firm aggregates, that is, cells that are monodisperse or grow in loose aggregates with only a few cells per aggregate. Suspension-competent cells include, without limitation, cells that grow in suspension without adaptation or manipulation (e.g., hematopoietic cells, lymphoid cells) and cells that have been made suspension-competent by gradual adaptation of attachment dependent cells (e.g., epithelial cells, fibroblast cells) to suspension growth.

In some embodiments, the host cells may include mutant or recombinant cells, including cells that express a qualitatively or quantitatively different spectrum of proteins that catalyze post-translational modification of proteins (for example, glycosylation enzymes such as glycosyl transferases and/or glycosidases, processing enzymes such as propeptides, including enzymes which promote the formation of functional vWF), relative to the cell type from which they were derived.

As one example, the host cell comprises an introduced polynucleotide that encodes at least one "processing factor" protein, where said polynucleotide is operably linked to at least one regulatory element and expresses the processing factor protein. The term "processing factor" includes any protein, peptide, non-peptide cofactor, substrate or nucleic acid which promotes the formation of a functional protein. Examples of processing factors include, but are not limited to paired basic amino acid converting enzyme (PACE), vitamin K-dependent epoxide reductase (VKOR), vitamin K-dependent gamma-glutamyl carboxylase (VKGC), or a combination thereof. Particular embodiments utilize the human sequence(s) for PACE, VKOR, and/or VKGC.

PACE, originally isolated from a human liver cell line, is a subtilisin-like endopeptidase, that is, a propeptide-cleaving enzyme which exhibits specificity for cleavage at basic residues of a protein (e.g., -Lys-Arg-, -Arg-Arg-, or -Lys-Lys-). The co-expression of PACE and a proprotein which requires processing for production of the mature protein results in high level expression of the mature protein.

For long-term, high-yield production of vWF, stable expression is generally preferred. For example, cell lines which stably express vWF may be transformed using expression vectors which may contain viral origins of replication and/or endogenous expression elements and a selectable marker gene on the same or on a separate vector. Following the introduction of the vector, cells may be allowed to grow for about 1-2 days in non-selective media before they are switched to selective media. The purpose of the selectable marker is to confer resistance to selection, and its presence allows growth and recovery of cells which successfully express the introduced sequences.

Resistant clones of stably transformed cells may be proliferated using tissue culture techniques appropriate to the cell type. Any number of selectable markers or systems may be used to recover or identify transformed or transduced cell lines, whether transient or stable. These include, but are not limited to, the herpes simplex virus thymidine kinase and adenine phosphoribosyltransferase genes which can be employed in tk- or aprt-cells, respectively. Also, antimetabolite, antibiotic or herbicide resistance can be used as the basis for selection; for example, dihydrofolate reductase (DHFR) confers resistance to methotrexate; npt confers resistance to the aminoglycosides, neomycin and G-418; and als or pat confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine.

Host cells transformed with a polynucleotide sequence coding for vWF may be cultured under conditions suitable for the expression and recovery of the vWF from the cell culture. Any chemically-defined cell culture medium may be used. Particular examples include serum-free culture media, protein-free media, chemically-defined culture media, and culture media that lack animal-derived components.

Exemplary cell culture media include, without limitation, Basal Medium Eagle (BME); CMRL-1066 Medium; Dulbecco's Modified Eagle's Medium (DMEM); Glasgow Minimum Essential Medium, GMEM; H-Y Medium (HybriMax®); Medium 199; Minimum Essential Medium Eagle (EMEM); NCTC Medium; Swim's S-77 Medium; and Williams Medium E. Click's Medium; MCDB media 131 and Iscove's Modified Dulbecco's Medium (IMDM). Also included is DMEM/Ham's Nutrient Mixture F-12 (50:50), which is frequently used as a base media for the development of proprietary and specialty media to culture CHO cells for biomanufacturing, and MCDB medium 302, which was developed for CHO cells.

In particular embodiments, the media is a serum-free DMEM/HAM's F12 based formulation supplemented with one or more of the following: (a) glutamine; for example, final concentration about 0.9 g/l, (b) ferric sulfate×7H2O, for example, at about 0.0006 g/l, (c) putrescine, ×2HCl, for example, at about 0.0036 g/l, (d) Vitamin K1, for example, at about 0.0025 g/l, (e) Synperonic; for example, at a final concentration of about 1 g/l, (f) Phenol red, for example, at about 0.008 g/l, (g) Ethanolamine, for example, at about 0.00153 g/l, and/or (h) Na-hydrogencarbonate, for example, at about 2 g/l.

In specific embodiments, the cell culture medium is a CD-CHO medium or a CD-CHO AGT™ medium or a CD OptiCHO™ AGT™ medium, which are commercially available (INVITROGEN®) or Pro-CHO™ or PowerCHO™ media (LONZA®). CH-CHO, CD-CHO AGT™, and CD OptiCHO™ AGT™ medium can be used as a chemically-defined medium, a protein-free medium, and/or a serum-free medium, and can be supplemented with L-glutamine, if desired. The $Ca^{2+}$ levels of 1× CD-CHO AGT™ medium without calcium supplementation can range from about 0.25-0.35 mM (as determined by atomic absorption spectroscopy).

As noted above, certain embodiments utilize a serum-free cell culture medium. One example includes a defined serum-free medium that is capable of growing a wide range of suspension and monolayer cells, and which includes a serum substitute composed of fetuin, transferrin, phosphatidylcholine (e.g., 1-oleoyl-2-palmitoyl-phosphatidylcholine), linoleic acid, and cholesterol. Another example includes a cell culture medium containing a sterol such as cholesterol, which is stabilized by a surfactant rather than serum products or phospholipid micelles, and optionally containing soluble carboxylic acids as fatty acid precursors to satisfy lipid requirements, and/or alcohols that are capable of promoting cell.

Certain embodiments employ a cell culture medium that lacks "animal-derived" components. As used herein "animal-derived" components may include any components that are produced in an intact animal (e.g., proteins isolated and purified from serum) or components produced by using components produced in an intact animal (e.g., an amino acid made by using an enzyme isolated and purified from an animal to hydrolyse a plant source material). By contrast, a protein which has the sequence of an animal protein (that is, the protein has a genomic origin in an animal) but which is produced in vitro in cell culture (e.g., in a recombinant yeast or bacterial cell, or in mammalian cell line, recombinant or not), in media lacking components that are produced in, and isolated and purified from an intact animal is not an "animal-derived" component. For example, a protein which has the sequence of an animal protein (that is, has a genomic origin in an animal) but which is produced in a recombinant cell in media lacking animal derived components is not an "animal-derived" component. Accordingly, a cell culture medium lacking animal-derived components is one that may contain animal proteins that are recombinantly produced; such medium, however, does not contain, for example, animal serum or proteins or other products purified from animal serum. Such medium may, for example, contain one or more components derived from plants.

Any cell culture medium that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. Media lacking animal-derived components and/or proteins are available from commercial suppliers, such as, for example, SIGMA®, SAFC, INVITROGEN®, GIBCO® or LONZA®.

For example, certain embodiments employ suspension cell culture techniques. Examples of suspension cell culture techniques include perfusion processes, batch processes (e.g., simple batch processes, fed-batch processes), and draw-fill processes.

In a suspension cell-perfusion process the cells are typically inoculated into a seed culture vessel containing a cell culture medium, which preferably lacks animal-derived components and is propagated until the cells reach a minimum density.

Subsequently, the propagated seed culture is then transferred to a large-scale culture vessel, which likewise contains a culture medium that preferably lacks animal-derived components. The cells are propagated until at least a predetermined cell density is reached. In this phase the cells are grown in suspension to allow the cell number within the culture vessel to increase to a predetermined or critical value.

Medium exchange can be performed by continuously perfusing the culture vessel with fresh medium while the recombinant cells are retained in the culture vessel. The amount of perfused medium may depend on the cell density and is typically from about 10-300%, preferably from about 10% to 95%, 25% to 80%, of the tank volume per day (24 hours).

In the growth phase the culture is propagated until the cells reach a certain density. Reaching this density, the culture enters the production phase.

When the cell density reaches the value suitable for initiation of production phase, about 60-95% of the tank medium in the tank is changed every 24 hours, preferably about 80%. An 80% medium exchange is also preferably used in the production phase. Set-points may also be changed at this point and set at values suitable for production of the respective protein. The medium perfusion is preferably performed continuously. The flow rate of medium can be expressed in terms of percentage tank volume of medium per defined period of time.

Medium perfusion may be from about 10-200% tank volume per 10-48 hours; preferably, the medium perfusion is about 90% per 10-48 hours, more preferably the medium perfusion is about 80% tank volume every 24 hours.

Cell retention within the culture vessel may be achieved using a number of cell retention devices. Different separation principles may be used for this process. The methods could be based on gravity settling, acoustic settling, centrifugal settling or filtration. The following sets of apparatus may all be used for this process: internal or external filters like internal or external spin filters (e.g. Spinfilter P from Sartorius), external cross flow filters, external or internal hollow fiber cartridge filters (e.g. alternating tangential flow (ATF) from Refine).

VWF multimers can vary from a simple dimer up to multimers consisting of more than 16 covalently linked vWF monomers. The different proteins forms do have different biological activities. For example low molecular weight multimers of vWF do have a lower ristocetin co-factor activity (vWF:RCoF), whereas high molecular weight forms of vWF do have a higher vWF:RCoF activity. A high vWF:RCoF activity of a vWF preparation correlates with a high activity in primary hemostasis as vWF preparations with high vWF:RCoF more efficiently contribute to the agglutination of platelets and to the tethering of platelets to collagen exposed by an injury. The ratio of vWF:RCoF over the antigen content (vWF:Ag) in human plasma is by definition 1.0.

It is thus desirable to manufacture pharmaceutical vWF preparations with a ratio of vWF:RCoF to vWF:Ag of at least 0.5, or at least 0.55, or at least 0.6, or at least 0.65 or at least 0.7, or at least 0.75, or at least 0.8, or at least 0.85, or at least 0.9, or at least 0.95 or at least 1.0.

In certain therapeutic situation it is also be preferable to manufacture vWF preparations which do have an increased vWF:RCoF/vWF:Ag ratio higher than that present in human plasma, for example of at least 1.05, or at least 1.1, or at least 1.15, or at least 1.2 or at least 1.25, or at least 1.3, or at least 1.35, or at least 1.40, or at least 1.45 or at least 1.50, or at least 1.55 or at least 1.60, or at least 1.65 or at least 1.70 or at least 1.75, or at least 1.80, or at least 1.85 or at least 1.90 or at least 1.95 or at least 2.0.

In order to manufacture pharmaceutical vWF preparations with increased vWF:RCoF/vWF:Ag ratios it is normally necessary to devise down-stream purification procedures which increase the amount of higher molecular weight multimers of vWF. This is often cumbersome and may result in decreased yield of vWF product as each down-stream purification step is usually associated with some product loss.

The inventors of the present invention have now surprisingly found that the enrichment of higher molecular weight multimers of vWF can already be achieved at the up-stream stage of manufacturing during cell culture by using a separation device which retains the desired high molecular weight multimeric forms of vWF in the bioreactor (retentate) whereas the less desired lower molecular weight forms of vWF pass the separation device (permeate). However, as the lower molecular weight forms of vWF still are capable of binding and of stabilizing Factor VIII, the fraction in the permeate may also be a product for certain specific uses like for the stabilization of Factor VIII. In the latter case the low molecular weight fraction of vWF multimers may be the desired vWF form.

Harvesting the fraction which is enriched in HMW vWF multimers can be either done i) at the end of the fermentation process or ii) concomitantly by using an additional separation device. This additional separation device in the case ii) could be any separation device separating the cells form the retentate and which does not further separate LMW vWF multimers from HMW vWF multimers. As result of such a fermentation process in case ii) a vWF preparation is obtained which is enriched in HMW vWF multimers and the residence time in the bioreactor is reduced in comparison to a fermentation process as in case i). Shortening the residence is beneficial in general in order to minimize degradation events.

However, if the ratio of vWF:RCoF/vWF:Ag is higher than 2.0 there is an increasing risk of thromboembolic complications when such preparations are administered to patients, as such ultra-large molecular weight multimers of vWF may lead to the agglutination of platelets in non-physiological situations.

If such ultra-large molecular weight multimers are present in the cell culture medium it may be beneficial to apply separation devices with a molecular weight cut off (MWCO) of 10,000,000 Da which retains the ultra-large multimers of vWF in the bioreactor (retentate) whereas the desired high-molecular weight forms of vWF are separated into the filtrate.

The inventors also have found a process for manufacturing a recombinant von Willebrand factor (vWF) by culturing host cells in a bioreactor in a cell culture medium, wherein the host cells produce recombinant vWF which is secreted into the cell culture medium and wherein the vWF in the cell culture medium comprises vWF multimers of different size, wherein at least one cell culture medium component is fed to the cell culture medium and wherein the cell culture comprising the cells, the recombinant vWF and the cell culture medium is pumped over a separation system and wherein the separation system separates the vWF multimers into at least a permeate fraction which is enriched in low molecular weight (LMW) multimers of vWF and reduced in high molecular weight (HMW) multimers of vWF as compared to the vWF multimers in the cell culture supernatant before separation and a retentate fraction which is reduced in low molecular weight (LMW) multimers of vWF and enriched in high molecular weight (HMW) multimers of vWF as compared to the vWF multimers in the cell culture supernatant before separation The HMW vWF Multimer Ratio is preferably equal or above 1.1, or above 1.2, or above 1.25, or above 1.30, or above 1.35, or above 1.40 or above 1.45 or above 1.50 or above 1.60, or above 1.70, or above 1.80, or above 1.90.

In a preferred embodiment the invention encompasses also a bioreactor comprising a cell culture medium comprising vWF multimers in a retentate and a cell culture medium comprising vWF multimers in a permeate wherein the HMW vWF Multimer Ratio is equal to or above 1.1, or above 1.2, or above 1.25, or above 1.30, or above 1.35, or above 1.40 or above 1.45 or above 1.50 or above 1.60, or above 1.70, or above 1.80, or above 1.90.

The LMW vWF Multimer Ratio in is preferably equal to or below 0.90, or below 0.85, or below 0.80, or below 0.75, or below 0.70 or below 0.65 or below 0.60, or below 0.55, or below 0.50.

A preferred embodiment of the invention encompasses also a bioreactor comprising a cell culture medium comprising vWF multimers and a cell culture medium comprising vWF multimers in a permeate wherein the LMW vWF Multimer Ratio is below 0.90, or below 0.85, or below 0.80, or below 0.75, or below 0.70 or below 0.65 or below 0.60, or below 0.55, or below 0.50.

By choosing the MWCOs of the separation device the man skilled in the art is enabled by the present invention to choose the molecular size of the vWF product which is then subsequently purified according to techniques well-known in the art.

Such separation of vWF multimers of different molecular weight already at the fermentation stage, i.e. during upstream processing, greatly facilitates separation in a subsequent post-fermentation or down-stream purification, as the desired fractions of vWF multimer are already enriched in the desired vWF multimers. Therefore potentially less purification steps are required in the down-stream processing resulting in faster processing time and higher yields. The invention usually also leads to higher purity of the resulting vWF preparation as part of the purification starts already in the bioreactor and subsequent downstream processing then start with a vWF already enriched for the desired molecular-weight fraction.

Certain embodiments may include culture methods that monitor and control certain parameters, such as pH, dissolved oxygen tension (DOT), and temperature. As one example, the pH can be controlled by regulating the $CO_2$ concentration in the headspace gas and/or sparger, and by addition of base to the culture medium when required. Certain embodiments therefore include large-scale production of a recombinant polypeptide in a cell culture medium, where the concentration of dissolved $CO_2$ in the culture is monitored and constant or intermittent sparging of air through the culture medium is employed to maintain certain concentration ranges of $CO_2$. In some aspects, the predetermined range for the concentration of dissolved $CO_2$ is about 80-200 mmHg, preferably about 100-180 mmHg, e.g., about 140 mmHg. In most instances, the sparging rate of the air is controlled in relation to the monitored concentration of dissolved $CO_2$ in the culture medium. For example, the sparging rate of air can be in the range of about 0.000-0.100 L/min per L of culture liquid, preferably about 0.005-0.020 L/min per L of culture liquid, particularly where the monitored concentration of dissolved $CO_2$ is equal to (predetermined) set-point concentration. In some instances, the sparging rate of air is in the range of 0.000-0.005, such as around 0.0 L/min per L of culture liquid when the monitored concentration of dissolved $CO_2$ is equal to the set-point concentration −5 mmHg; and in the range of 0.010-0.100 L/min per L of culture liquid when the monitored concentration of dissolved $CO_2$ is equal to the set-point concentration +5 mmHg (see U.S. Application No. 2006/0216790). Such methods can be used to maintain a desired pH in the cell culture medium, for example, where any solid or liquid substances added to the culture medium do not give rise to a localized pH value of above about 7.5.

Dissolved oxygen tension may be maintained, for instance, by sparging with air or pure oxygen or mixtures thereof. The temperature-control medium is typically water or other liquid, heated or cooled as necessary. In certain aspects, the water may be passed through a jacket surrounding the vessel or through a piping coil immersed in the culture.

The vWF produced by a recombinant cell can be purified and characterized according to a variety of techniques known in the art. Exemplary systems for performing protein purification and analyzing protein purity include fast protein liquid chromatography (FPLC) (e.g., ÄKTA and Bio-Rad FPLC systems), hydrophobic interaction chromatography, and high-pressure liquid chromatography (HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., Coomassie, silver stain), preparative isoelectric focusing (IEF), immunoblot, Bradford, differential solubility (e. g., ammonium sulfate precipitation) and ELISA, which may be utilized during any step of the production or purification process, typically to measure the purity of the protein composition.

In certain aspects, the recombinant vWF can be subjected to multiple chromatographic purification steps, including any combination of affinity chromatography, ion-exchange chromatography, hydrophobic interaction chromatography, dye chromatography, hydroxyapatite chromatography, size exclusion chromatography and preferably immunoaffinity chromatography, mainly to concentrate the desired protein and to remove substances which may cause fragmentation, activation and/or degradation of the recombinant protein during manufacture, storage and/or use. Illustrative examples of such substances that are preferably removed by purification include other protein contaminants, such as modification enzymes like PACE/furin, VKOR, and VKGC; proteins, such as host cell proteins, which are released into the tissue culture media from the production cells during recombinant protein production; non-protein contaminants, such as lipids; and mixtures of protein and non-protein contaminants, such as lipoproteins. Purification procedures for vWF proteins are known in the art (see for example WO 2011/022657).

In order to minimize the theoretical risk of virus contaminations, additional steps may be included in the process that allow effective inactivation or elimination of viruses. Such steps include, for example, heat treatment in the liquid or solid state, treatment with solvents and/or detergents, radiation in the visible or UV spectrum, gamma-radiation, and nanofiltration.

Pharmaceutical Compositions

Embodiments of the present invention include proteins and preferably vWF proteins that are produced according to the methods provided herein, and formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the modulatory or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, subcutaneous, and intramuscular administration and formulation.

In certain applications, the pharmaceutical or therapeutic compositions of the invention do not stimulate an immune reaction. In some aspects, the pharmaceutical composition comprising the protein(s) may be formulated in stable liquid form. In other aspects, the pharmaceutical composition may be formulated in lyophilized form; protein(s) may be lyophilized by a variety of procedures known in the art. Lyophilized formulations are typically reconstituted prior to use by the addition of one or more pharmaceutically acceptable diluents such as sterile water for injection or sterile physiological saline solution.

In certain embodiments, the proteins have a solubility that is desirable for the particular mode of administration, such a s intravenous administration. Examples of desirable solubilities include at least about 1 mg/ml, at least about 10 mg/ml, at least about 25 mg/ml, and at least about 50 mg/ml.

In certain circumstances it will be desirable to deliver the pharmaceutical compositions disclosed herein parenterally, subcutaneously, intravenously, intramuscularly, intra-arterially, intrathecally, intraparenchymally, intraventricularly, intraurethrally, intrasternally, intracranially, intrasynovially, or even intraperitoneally). Suitable devices for parenteral administration include needle (including micro-needle) injectors, needle-free injectors, and infusion techniques.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art.

Typically, such compositions are prepared as injectables, either as liquid solutions or suspensions; solid forms suitable for solution in or suspension in liquid prior to injection can also be prepared. The preparation can also be emulsified.

The pharmaceutical compositions may be formulated to be immediate and/or sustained release. Sustained release compositions include delayed, modified, pulsed, controlled, targeted and programmed release.

Methods of formulation are well known in the art. The recombinant proteins provided herein may be administered accordingly to any therapeutically effective dosing regimen. The dosage amount and frequency can be selected to create an effective amount of the protein(s) and minimize harmful effects. The effective amount will depend on a variety of factors, including the route of administration, the type of subject being treated, and the physical characteristics of the subject under consideration, such as weight, diet, concurrent medication and other factors that persons skilled in the medical arts will recognize.

Formulations of vWF have been described for example in WO 2010/048275.

All publications, patent applications, and issued patents cited in this specification are incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

All fermentations were performed using a Sartorius Biostat B-DCU Controller to control the pH at 7.0, the DO at 30% air saturation, the temperature and a stirrer speed of 150 rpm. The process was executed in a Sartorius B vessel with a working volume of 5 L. After the inoculation of the reactor a growth phase at 37° C. was performed, followed by a production phase at 33° C. All processes were performed with the same CHO-cell line expressing a wild-type full length vWF fused at its C-terminal end to human wild-type full-length albumin protein. The cell line was obtained as described in WO 2009/156137.

Example 1

Batch Process, Comparative Example

A batch-process running with CSL-DBM-PFCDM-media (SAFC) was started with a cell density of $4.4*10^5$ cells/mL. After 7 days a cell density of $6.9*10^6$ cells/mL was reached. A sample from the bioreactor was taken daily and the vWF activity (vWF:RCoF) and antigen (vWF:Ag) was determined. From these measurements the ratio vWF:RCoF/vWF:Ag was calculated. FIG. 1 shows that this ratio is slightly decreasing after reaching a peak level at about day 2.

Example 2

Process of the Invention

The retention module, an ATF 4 (Refine Technology) was operated with an exhaust flow rate of 3 L/min and a pressure flow rate of 3 L/min. A 750 kDa Molecular Weight Cut-Off (MWCO) hollow fiber membrane obtained from GE Healthcare Life Sciences operated in ATF flow mode was used to enrich the high molecular weight (HMW) vWF in the bioreactor and to reduce the low molecular weight (LMW) vWF in the bioreactor. A CD CHO (Gibco) based culture media was used during growth phase and also as feed media. The culture was started with $5*10^5$ cells/mL. After a growth phase (data not shown) of 4 days the ATF was started with a harvest rate for permeate of about 100% of the tank volume per day. At this time the cell density in the bioreactor was $3.8*10^6$ cells/mL. When the cell density reached $7*10^6$ cells/mL the temperature was shifted from 37° C. to 33° C. for the production phase.

Figure 2:
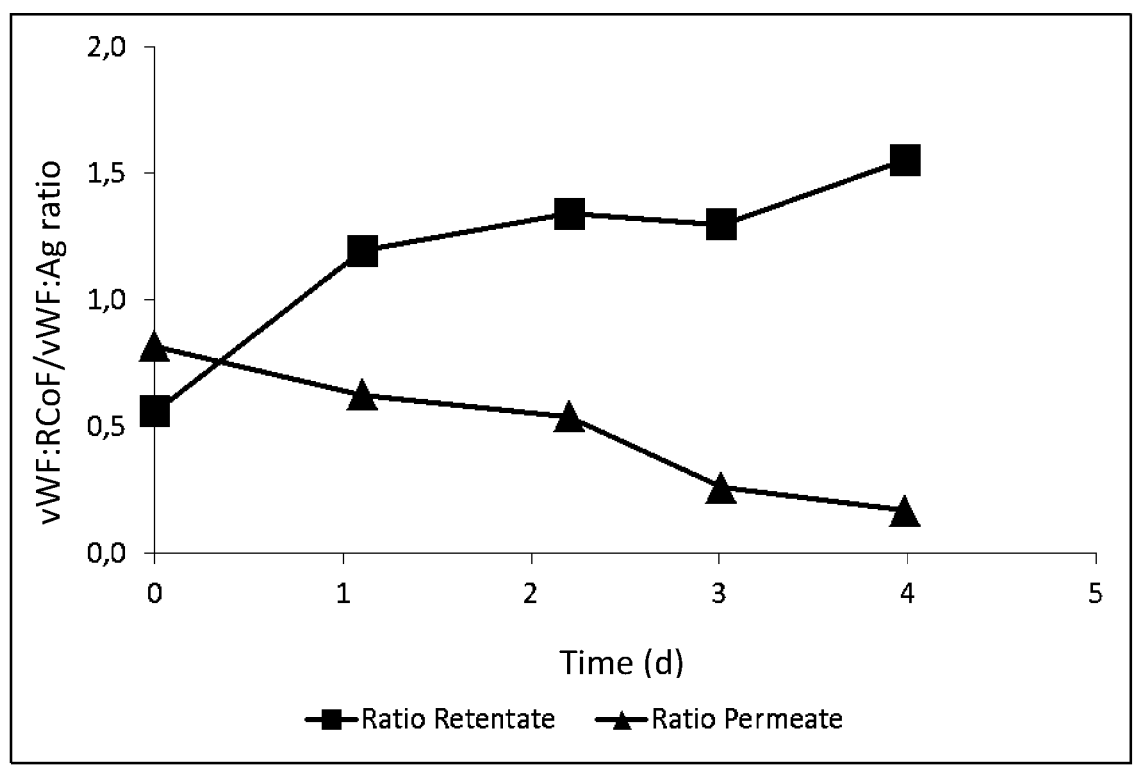
FIG. 2 shows the ratio of vWF Ristocetin Cofactor activity over vWF antigen (vWF:RCoF/vWF:Ag) in the retentate (bioreactor) and in the permeate during the process of Example 2.

A sample from the bioreactor and of the permeate was taken daily and the vWF ristocetin cofactor activity (vWF:RCoF) and vWF antigen (vWF:Ag) was determined. From these measurements the ratio vWF:RCoF/vWF:Ag was calculated. It was shown that due to the removal of the LMW vWF the ratio vWF:RCoF/vWF:Ag in the retentate (bioreactor) was rising, whereas the ratio vWF:RCoF/vWF:Ag in the permeate was decreasing due to the removal of the HMW vWF (FIG. 2).

Figure 3:
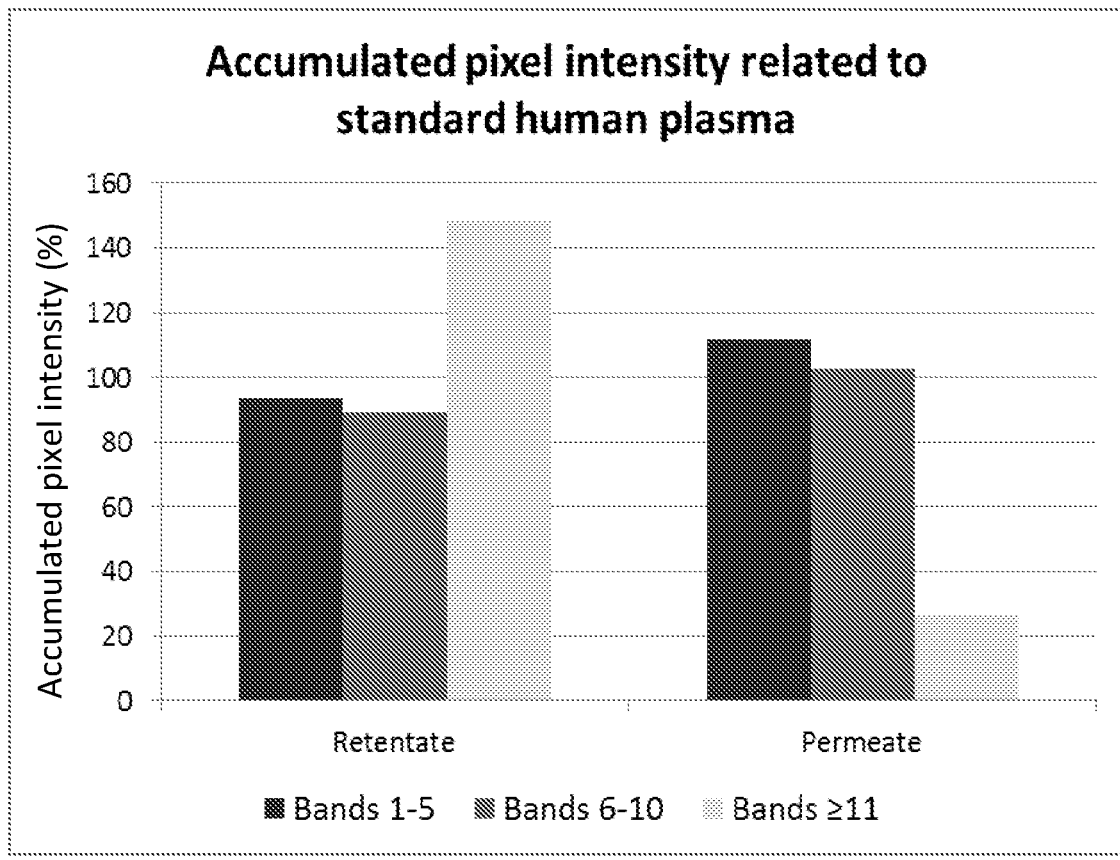
FIG. 3 shows the accumulation of HMW vWF in the retentate (bioreactor) and the depletion of HMW vWF in the permeate at day 4 in Example 2. The accumulated pixel intensities related to standard human plasma of bands 1-5, 6-10 and >11 were determined as described in Example 2.

A vWF multimer analysis (multimer electrophoresis) was performed at day 4 according to Ott et al. (Am J Clin Pathol 2010; 133:322-330) to show the enrichment of high-molecular-weight vWF in the retentate (bioreactor) and the separation and removal of low-molecular-weight vWF in the permeate. In addition to the multimer analysis of samples of the retentate and of the permeate a multimer analysis of a sample of standard human plasma (SHP) (Siemens, Standard Human Plasma, ORKL17) was performed according to Ott et al. (Am J Clin Pathol 2010; 133:322-330) and used as a reference in each individual blot. The "accumulated pixel intensity related to standard human plasma" was then calculated by dividing the pixel intensity separately for each for the band sections 1-5, 6-10 and >11 in the respective sample by the average pixel intensity of the corresponding band sections of standard human plasma, wherein both individual accumulated pixel intensities were determined according to Ott et al. (Am J Clin Pathol 2010; 133:322-330) (Table 2, FIG. 3).

TABLE 2

| (vWF multimer analysis): | | | |
|---|---|---|---|
| | Accumulated pixel intensity related to standard human plasma of bands ≥11 | Accumulated pixel intensity related to standard human plasma of bands 6-10 | Accumulated pixel intensity related to standard human plasma of bands 1-5 |
| Retentate | 148.1 | 89.3 | 93.7 |
| Permeate | 26.6 | 102.8 | 111.9 |
| Ratio Retentate/Permeate | 5.568 | 0.869 | 0.837 |

Example 3

Process of the Invention

The retention module, an ATF 4 (Refine Technology) was operated with an exhaust flow rate of 3 L/min and a pressure flow rate of 3 L/min. A 750 kDa Molecular Weight Cut-Off (MWCO) hollow fiber membrane obtained from GE Healthcare Life Sciences operated in ATF flow mode was used to enrich the HMW vWF in the bioreactor and reduce the LMW vFW in the bioreactor. A PowerCHO-3 based cell culture medium (Lonza) was used for the entire process. The culture was started with $4*10^5$ cells/mL. After a growth phase (data not shown) of 3 days the ATF was started with a harvest rate for permeate of about 100% of the tank volume per day. At this time the cell density in the bioreactor was $1.4*10^6$ cells/mL. When the cell density reached $1.7*10^6$ cells/mL the temperature was shifted from 37° C. to 33° C. for the production phase.

Figure 4:
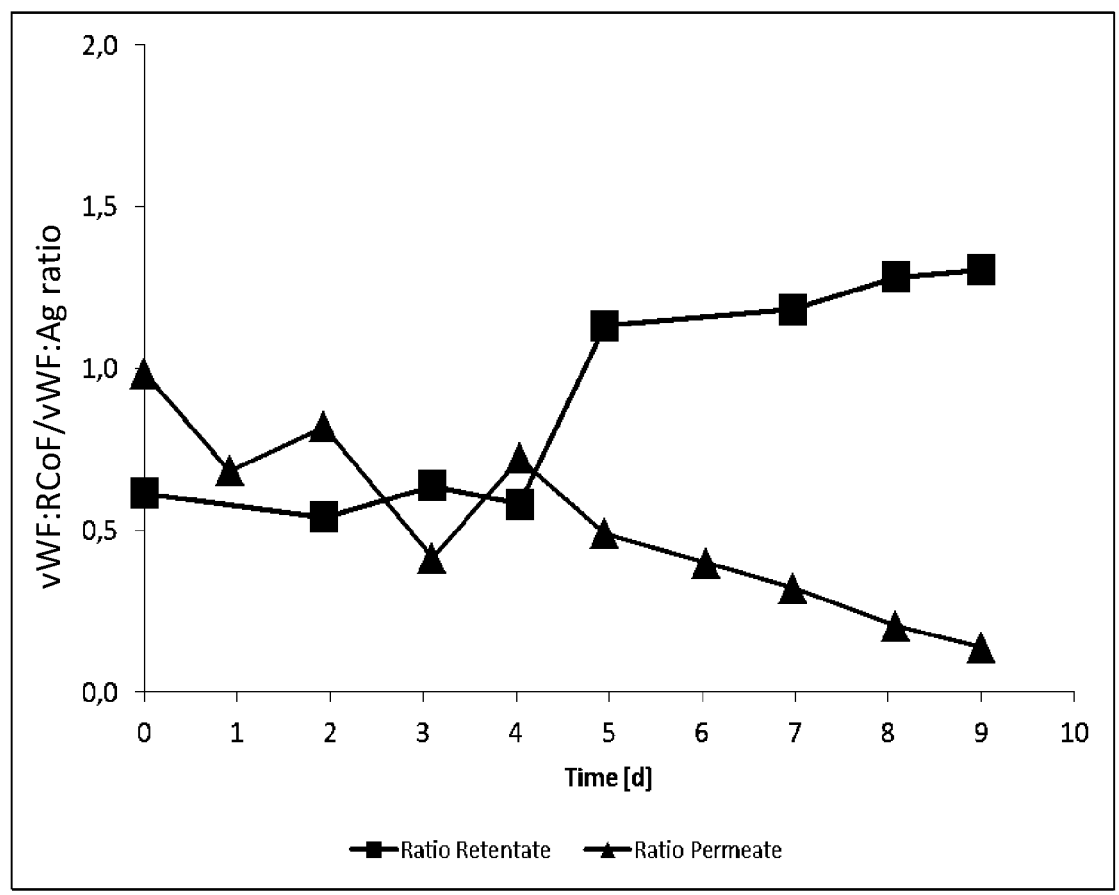
FIG. 4 shows the ratio of vWF Ristocetin Cofactor activity over vWF antigen (vWF:RCoF/vWF:Ag) in the retentate (bioreactor) and in the permeate during the process of Example 3.

A sample from the bioreactor and of the permeate was taken daily and the activity (vWF:RCoF) and antigen (vWF:Ag) were determined as described in Example 1. From these measurements the ratio vWF:RCoF/vWF:Ag was calculated. It was shown that due to the removal of the LMW vWF the ratio vWF:RCoF/vWF:Ag in the retentate (bioreactor) was rising, whereas the ratio vWF:RCoF/vWF:Ag in the permeate was decreasing due to the removal of the HMW vWF (FIG. 4).

At the end of the process a multimer electrophoresis was performed to show the accumulation of high-molecular-weight vWF in the bioreactor and the separation/removal of low-molecular-weight vWF with the permeate. The accumulated pixel intensity related to standard human plasma was calculated as above.

Figure 5:
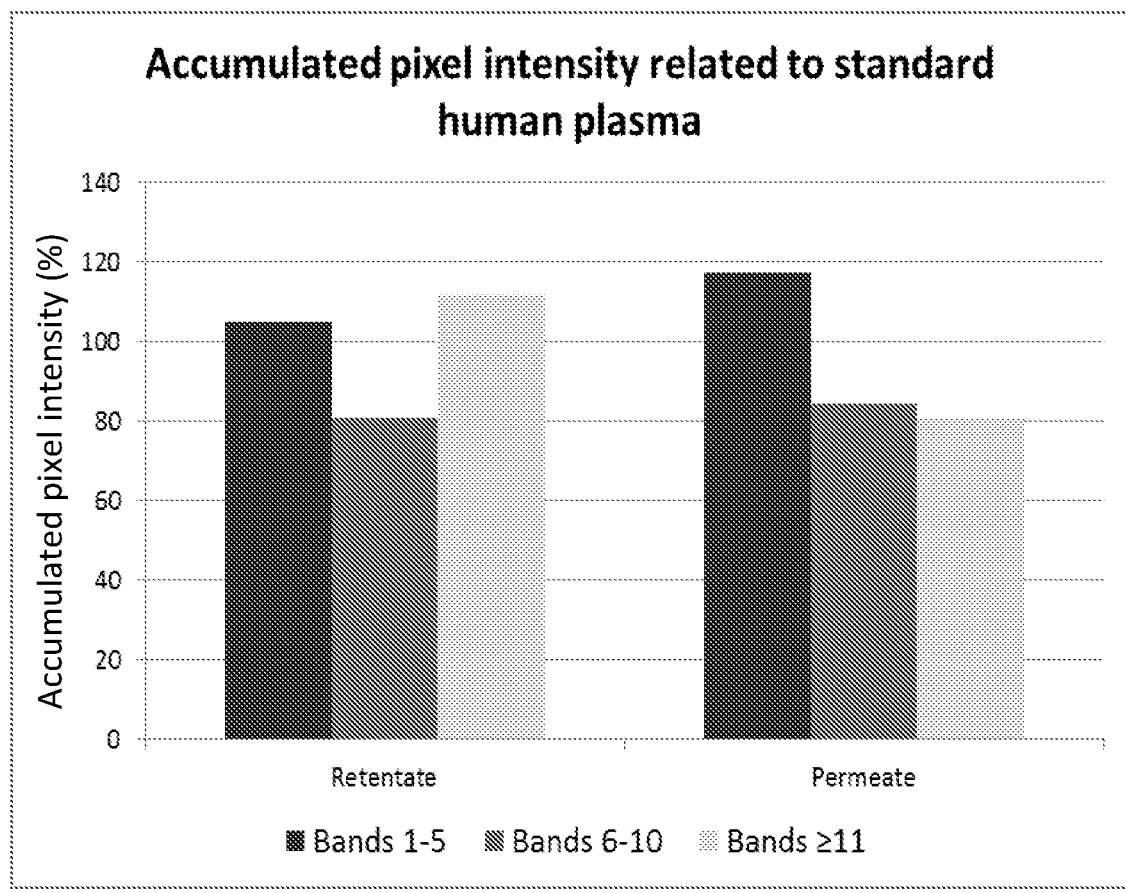
FIG. 5 shows the accumulation of HMW vWF in the retentate (bioreactor) and the depletion of HMW vWF in the permeate at day 9 in Example 3. The accumulated pixel intensities related to standard human plasma of bands 1-5, 6-10 and >11 were determined as described in Example 2.

A vWF multimer analysis (multimer electrophoresis) was performed at day 9 according to Ott et al. (Am J Clin Pathol 2010; 133:322-330) to show the enrichment of high-molecular-weight vWF in the retentate (bioreactor) and the separation and removal of low-molecular-weight vWF in the permeate. In addition to the multimer analysis of samples of the retentate and of the permeate a multimer analysis of a sample of standard human plasma (SHP) (Siemens, Standard Human Plasma, ORKL17) was performed according to Ott et al. (Am J Clin Pathol 2010; 133:322-330) and used as a reference in each individual blot. The "accumulated pixel intensity related to standard human plasma" was then calculated as described in Example 2 (Table 3, FIG. 5).

TABLE 3

(vWF multimer analysis):

| | Accumulated pixel intensity related to standard human plasma of bands ≥11 | Accumulated pixel intensity related to standard human plasma of bands 6-10 | Accumulated pixel intensity related to standard human plasma of bands 1-5 |
|---|---|---|---|
| Retentate | 111.9 | 80.9 | 105.0 |
| Permeate | 80.8 | 84.4 | 117.3 |
| Ratio Retentate/Permeate | 1.385 | 0.959 | 0.895 |

Example 4

Another aspect of the inventions is a process wherein the retentate as obtained in any of Examples 2 and 3 is directly harvested from the bioreactor using an additional separation device. The separation device in this case could be any separation device separating the cells from the retentate and which does not further separate LMW vWF multimers from HMW vWF multimers. Bioreactor conditions and media are as described in previous examples.

As result of such a fermentation process a vWF preparation is obtained which is enriched in HMW vWF multimers and the residence time in the bioreactor is reduced. Furthermore this kind of process is not limited in process time because of no accumulation of vWF multimers occurs.

Example 5

Figure 6:
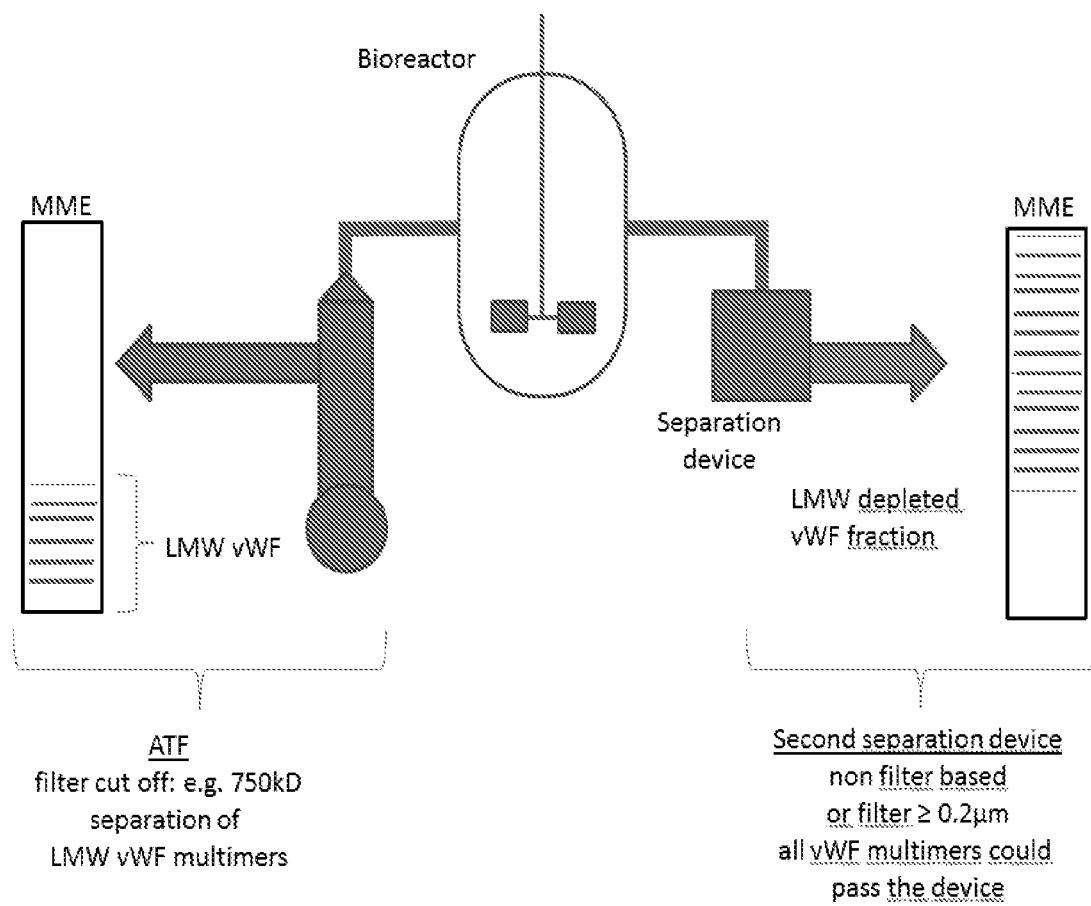
FIG. 6 shows a schematic drawing of the hypothetical process setup of Example 4.
Figure 7:
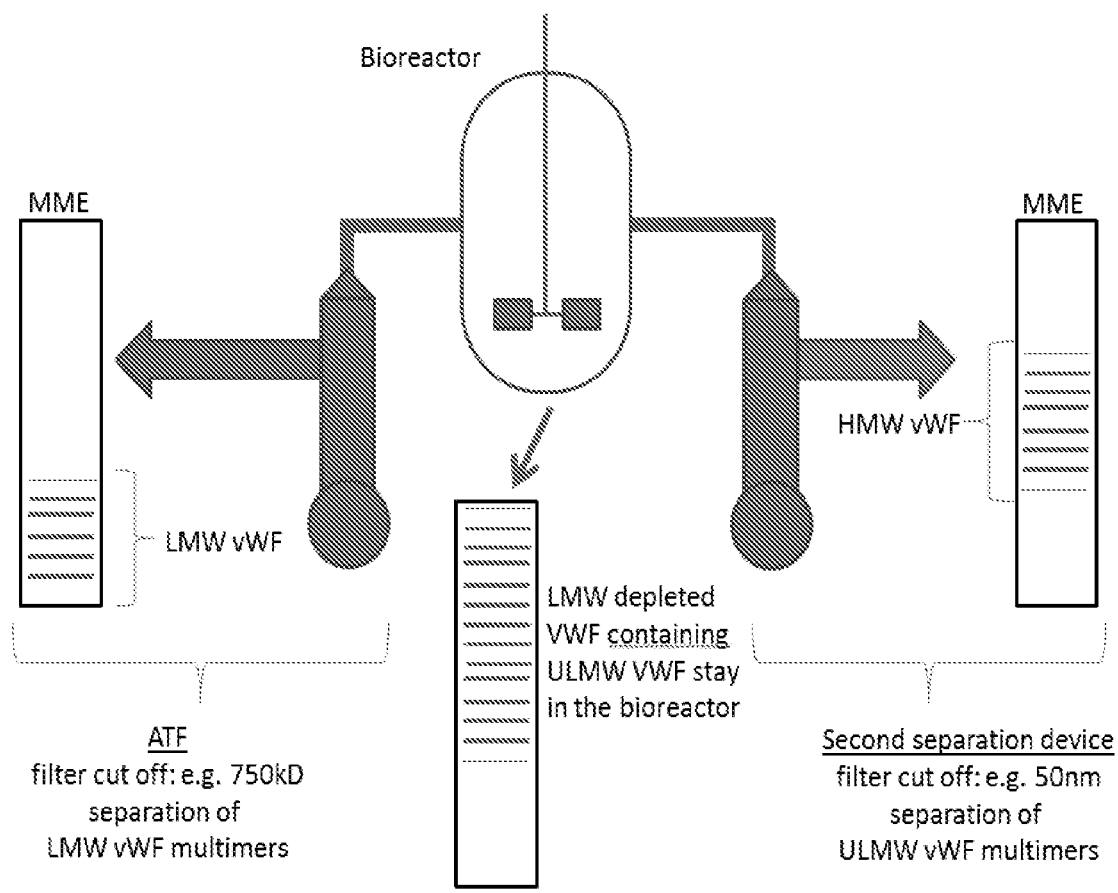
FIG. 7 shows a schematic drawing of the hypothetical process setup of Example 5.

Another aspect of the inventions is a process wherein the retentate as obtained in any of Examples 2 and 3 is then additionally subjected to a second separation wherein now the ultra-large vWF multimers (ULMW vWF multimers) are enriched in the retentate, providing a second permeate in which the proportion of ultra-large vWF multimers in the total vWF multimer amount is reduced as compared to the proportion of ultra-large vWF multimers in the total vWF multimer amount in the retentate before said second separation. Bioreactor conditions and media are as described in previous examples. A second ATF system is connected to the bioreactor (FIG. 6) which is equipped with a hollow fiber membrane of MWCO of about 10,000,000 Da or 0.1 μm. By harvesting the permeate of the second separation system with a flow rate of 20-200% of the tank volume the ULMW vWF multimers is removed.

As a result of such a fermentation comprising a first separation leading to an enrichment of the HMW multimers of vWF with a second separation leading to a depletion of the HMW multimers from ULMW vWF multimers generates a VWF preparation in the permeate of the second separation which is depleted both for LMW vWF multimers and for ULMW vWF multimers, then having both high activity in primary hemostasis but avoiding possible adverse effects by the presence of ULMW vWF multimers.

The two separations can be done in parallel or sequentially.

Example 6

Process of the Invention

The fermentation was performed using a Sartorius Biostat B-DCU Controller to control the pH at 7.0, the DO at 30% air saturation, the temperature and a stirrer speed of 150 rpm. The process was executed in a Sartorius B vessel with a working volume of 5 L.

After the inoculation of the reactor a growth phase at 37° C. was performed, followed by a production phase at 33.5° C. The process was performed with a CHO-cell line expressing a wild-type full length vWF (NCBI Sequence NP_000543). The cell line was obtained as described in WO 2009/156137.

The retention module, an ATF 4 (Refine Technology) was operated with an exhaust flow rate of 3 L/min and a pressure flow rate of 3 L/min. A 750 kDa Molecular Weight Cut-Off (MWCO) hollow fiber membrane obtained from GE Healthcare Life Sciences operated in ATF flow mode was used to enrich the high molecular weight (HMW) vWF in the bioreactor and to reduce the low molecular weight (LMW) vWF in the bioreactor.

A CD CHO (Gibco) based culture media was used during growth phase and also as feed media. The culture was started with $7.6*10^5$ cells/mL.

Figure 9:
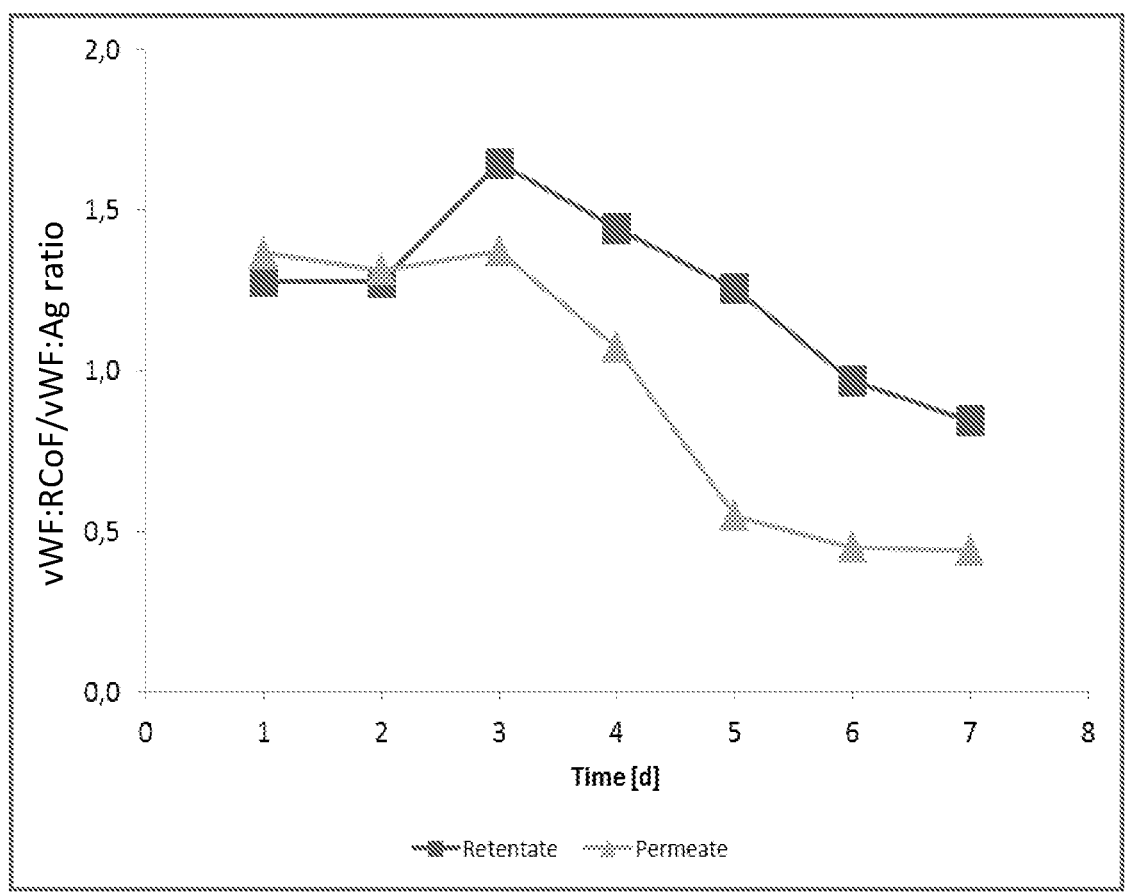
FIG. 9 shows the ratio of vWF Ristocetin Cofactor activity over vWF antigen (vWF:RCoF/vWF:Ag) in the retentate (bioreactor) and in the permeate during the process of Example 6 as described in Example 2.

After a growth phase (data not shown) of 1 day the ATF was started with a harvest rate for permeate of about 100% of the tank volume per day. Additionally the temperature was shifted from 37° C. to 33.5° C. for the entire production phase. At this time the cell density in the bioreactor was $10.9*10^5$ cells/mL. At day 7 the cell density reached $70.0*10^5$ cells/mL A sample from the bioreactor and of the permeate was taken daily and the vWF ristocetin cofactor activity (vWF:RCoF) and vWF antigen (vWF:Ag) was determined. From these measurements the ratio vWF:RCoF/vWF:Ag was calculated. It was shown that due to the removal of the LMW vWF the ratio vWF:RCoF/vWF:Ag in the retentate (bioreactor) was rising, whereas the ratio vWF:RCoF/vWF:Ag in the permeate was decreasing due to the removal of the HMW vWF (FIG. 9).

Figure 8:
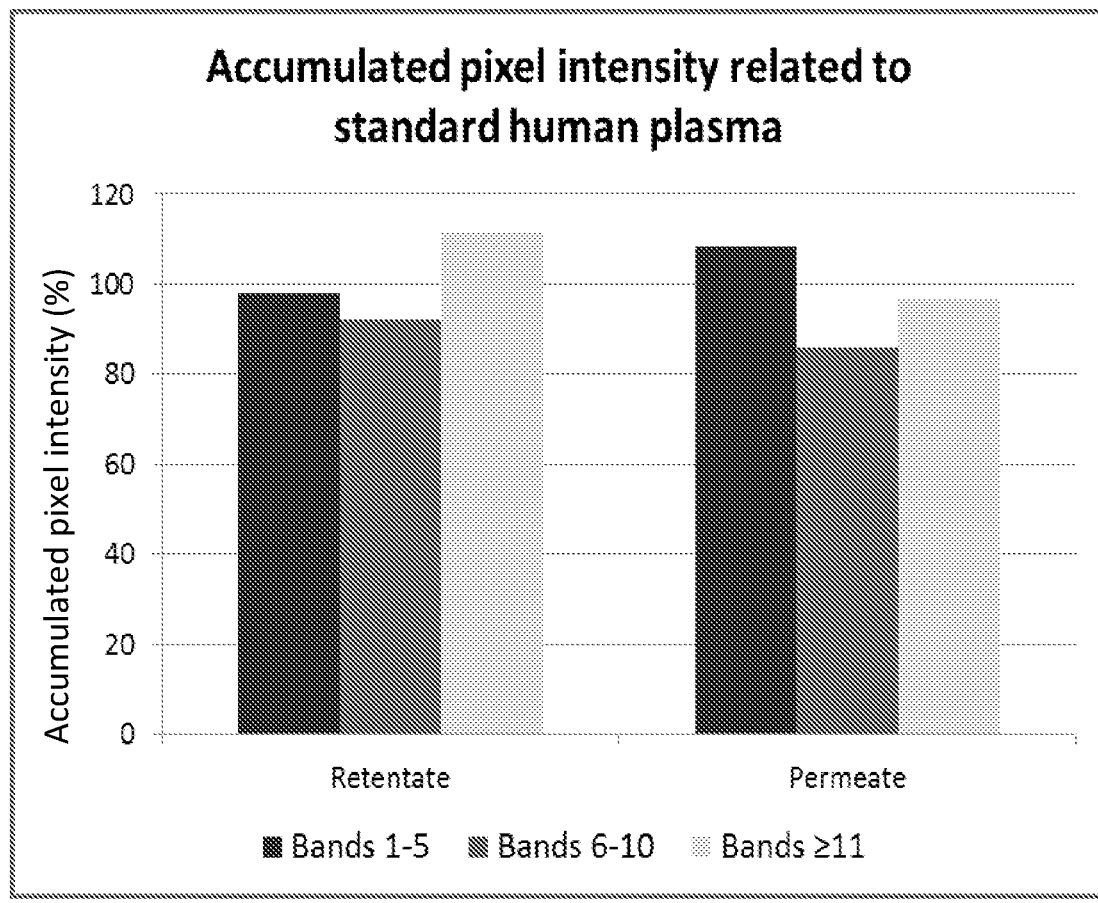
FIG. 8 shows the accumulation of HMW vWF in the retentate (bioreactor) and the depletion of HMW vWF in the permeate at day 7 of Example 6. The accumulated pixel intensities related to standard human plasma of bands 1-5, 6-10 and >11 were determined as described in Example 2.

A vWF multimer analysis (multimer electrophoresis) was performed at day 7 according to Ott et al. (Am J Clin Pathol 2010; 133:322-330) to show the enrichment of high molecular-weight vWF in the retentate (bioreactor) and the separation and removal of low-molecular-weight vWF in the permeate. In addition to the multimer analysis of samples of the retentate and of the permeate a multimer analysis of a sample of standard human plasma (SHP) (Siemens, Standard Human Plasma, ORKL17) was performed according to Ott et al. (Am J Clin Pathol 2010; 133:322-330) and used as a reference in each individual blot. The "accumulated pixel intensity related to standard human plasma" was then calculated by dividing the pixel intensity separately for each for the band sections 1-5, 6-10 and >11 in the respective sample by the average pixel intensity of the corresponding band sections of standard human plasma, wherein both individual accumulated pixel intensities were determined according to Ott et al. (Am J Clin Pathol 2010; 133:322-330) (Table 4, FIG. 8).

TABLE 4

| | (vWF multimer analysis): | | |
|---|---|---|---|
| | Accumulated pixel intensity related to standard human plasma of bands ≥11 | Accumulated pixel intensity related to standard human plasma of bands 6-10 | Accumulated pixel intensity related to standard human plasma of bands 1-5 |
| Retentate | 111.54 | 92.2 | 97.9 |
| Permeate | 96.44 | 86.0 | 108.4 |
| Ratio Retentate/ Permeate | 1.16 | 1.07 | 0.90 |

The invention claimed is:

1. A process for manufacturing a recombinant von Willebrand factor (vWF), comprising
    (a) culturing a cell culture of host cells in a bioreactor in a cell culture medium, wherein the host cells produce recombinant vWF which is secreted into the cell culture medium and wherein the secreted recombinant vWF in the cell culture medium comprises vWF multimers of different sire, wherein at least one cell culture medium component is fed to the cell culture medium, and
    (b) pumping the cell culture comprising the host cells, the recombinant vWF, and the cell culture medium over a separation system having a molecular weight cut off size of about 750,000 Da, wherein the separation system separates the vWF multimers into at least
        (i) a permeate fraction which is enriched in low molecular weight (LMW) multimers of vWF and reduced in high molecular weight (HMW) multimers of vWF as compared to the vWF multimers in the cell culture supernatant before separation, and
        (ii) a retentate fraction which is reduced in multimers of vWF and enriched in multimers of vWF as compared to the vWF multimers in the cell culture supernatant before separation, and
    wherein the LMW multimers of vWF corresponds to bands 1 to 5 and the HMW multimers of vWF corresponds to bands 11 and higher as determined in a densitometric vWF analysis.

2. The process according to claim 1, further comprising harvesting the permeate fraction.

3. The process according to claim 2, wherein the separation system produces a LMW vWF Multimer Ratio that is equal to or below 0.9.

4. The process according to claim 1, further comprising harvesting the retentate fraction.

5. The process according to claim 4, wherein the separation system produces a HMW vWF Multimer Ratio that is equal to or above 1.1.

6. The process according to claim 5, wherein the recombinant vWF in the retentate fraction has a vWF:RCoF/vWF:Ag ratio above 1.2.

7. The process according to claim 1, wherein the recombinant vWF is a fusion protein and wherein vWF is fused to albumin or an Fc fragment of an immunoglobulin.

8. The process according to claim 1, further comprising subjecting the retentate fraction to a second separation, wherein the second separation produces a second permeate fraction and a second retentate fraction, wherein a proportion of ultra-large vWF multimers is enriched in the second retentate fraction and reduced in the second permeate fraction relative, to the proportion of ultra-large, vWF multimers in the total amount of vWF multimer in the retentate fraction before the second separation.

9. The process according to claim 8, wherein the second separation is performed in parallel with the first separation.

10. The process according to claim 8, wherein the second separation is performed after the first separation.

11. The process according to claim 8, wherein the second separation has a molecular weight cut off size of about 10,000,000 Da.

12. The process according to claim 1, wherein the separation system enriches HMW multimers of vWF in the bioreactor and reduces LMW multimers of vWF in the bioreactor.

* * * * *

UNITED STATES PATENT AND TRADEMARK OFFICE
CERTIFICATE OF CORRECTION

PATENT NO. : 10,829,539 B2
APPLICATION NO. : 15/316870
DATED : November 10, 2020
INVENTOR(S) : Stefan Debus and Holger Lind It is certified that error appears in the above-identified patent and that said Letters Patent is hereby corrected as shown below:

Claim 1, Column 75, Line 9, "different sire" should read --different size--.

Claim 1, Column 75, Line 21, "a retentate fraction which is reduced in multimers" should read --a retentate fraction which is reduced in LMW multimers--.

Claim 1, Column 75, Line 22, "and enriched in multimers" should read --and enriched in HMW multimers--.

Claim 8, Column 76, Line 18, "relative, to the proportion of ultra-large, vWF multimers" should read --relative to the proportion of ultra-large vWF multimers--.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*